United States Patent
Singh et al.

(10) Patent No.: US 11,378,552 B2
(45) Date of Patent: Jul. 5, 2022

(54) MICROSCALE PHOTOACOUSTIC SPECTROSCOPY, IMAGING, AND MICROSCOPY

(71) Applicant: Massachusetts Institute of Technology, Cambridge, MA (US)

(72) Inventors: Robin Singh, Cambdrige, MA (US); Anuradha M. Agarwal, Weston, MA (US); Brian Anthony, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 130 days.

(21) Appl. No.: 16/893,612

(22) Filed: Jun. 5, 2020

(65) Prior Publication Data
US 2020/0386718 A1    Dec. 10, 2020

Related U.S. Application Data

(60) Provisional application No. 62/858,351, filed on Jun. 7, 2019.

(51) Int. Cl.
*G01N 29/24* (2006.01)
*G01N 21/17* (2006.01)
(Continued)

(52) U.S. Cl.
CPC ....... *G01N 29/2418* (2013.01); *A61B 5/0095* (2013.01); *A61B 8/14* (2013.01); *G01N 21/1702* (2013.01); *G01N 2021/1706* (2013.01)

(58) Field of Classification Search
CPC .......... G01N 29/2418; G01N 21/1702; G01N 21/4795; G01N 2021/1706; G01N 2201/06113
See application file for complete search history.

(56) References Cited

U.S. PATENT DOCUMENTS

| | | |
|---|---|---|
| 8,538,214 B2 | 9/2013 | Chen et al. |
| 9,513,260 B2 | 12/2016 | Zhang et al. |

(Continued)

OTHER PUBLICATIONS

Arbabi et al., "Fundamental limits of ultrathin metasurfaces." Scientific Reports 7 (2017): 43722. 9 pages.

(Continued)

*Primary Examiner* — Suman K Nath
(74) *Attorney, Agent, or Firm* — Smith Baluch LLP

(57) ABSTRACT

A microscale photoacoustic sensor uses the detection of ultrasound waves generated by a sample in response to incident light absorption to perform photoacoustic spectroscopy, imaging, and microscopy. The microscale photoacoustic sensor, including components to excite a sample and detect ultrasound waves, may be integrated onto a single chip. The microscale photoacoustic sensor may excite a sample using a metasurface collimator. The metasurface collimator includes an array of diffraction grooves to collimate an excitation beam uniformly out of the plane of the sensor to create a wide and homogeneous beam spot. The microscale photoacoustic sensor may detect ultrasound waves using an optical photoacoustic transducer. The optical photoacoustic transducer includes a resonator on a mechanical membrane to detect ultrasound waves with high sensitivity. The microscale photoacoustic sensor may be used in applications such as deep-tissue neural imaging or microfluidic biological screening.

23 Claims, 21 Drawing Sheets

(51) Int. Cl.
*A61B 5/00* (2006.01)
*A61B 8/14* (2006.01)

(56) References Cited

U.S. PATENT DOCUMENTS

| | | | |
|---|---|---|---|
| 2009/0008536 A1* | 1/2009 | Hartog | G01J 3/4412 |
| | | | 250/227.14 |
| 2009/0156932 A1 | 6/2009 | Zharov | |
| 2013/0085398 A1 | 4/2013 | Roukes | |
| 2017/0106204 A1 | 4/2017 | Segev et al. | |
| 2018/0028117 A1 | 2/2018 | Desjardins et al. | |
| 2020/0203916 A1* | 6/2020 | Iguchi | G01N 21/3504 |

OTHER PUBLICATIONS

Baets et al., "Spectroscopy-on-chip applications of silicon photonics." Integrated optics: Devices, materials, and technologies XVII. vol. 8627. International Society for Optics and Photonics, 2013. 11 pages.
Boerkamp et al., "On-chip optical trapping and Raman spectroscopy using a TripleX dual-waveguide trap." Optics Express 22.25 (2014): 30528-30537.
Chen et al., "On-chip ultra-thin layer chromatography and surface enhanced Raman spectroscopy." Lab on a Chip 12.17 (2012): 3096-3102.
Frellsen et al., "Topology optimized mode multiplexing in silicon-on-insulator photonic wire waveguides." Optics Express 24.15 (2016): 16866-16873.
Graydon, "Topological data analysis." Nature Photonics 12.4 (2018): 189. 34 pages.
International Search Report and Written Opinion in International Patent Application No. PCT/US2020/036253 dated Sep. 9, 2020, 12 pages.
Jiang et al., "Parallel microgenetic algorithm design for photonic crystal and waveguide structures." Optics Letters 28.23 (2003): 2381-2383.
Liapis et al., "On-chip spectroscopy with thermally tuned high-Q photonic crystal cavities." Applied Physics Letters 108.2 (2016): 021105.18. 5 pages.
Marchetti et al., "High-efficiency grating-couplers: demonstration of a new design strategy." Scientific Reports 7.1 (2017): 16670. 8 pages.
Michaels et al., "Leveraging continuous material averaging for inverse electromagnetic design." Optics Express 26.24 (2018): 31717-31737.
Molesky et al., "Inverse design in nanophotonics." Nature Photonics 12.11 (2018): 659. 12 pages.
Pang et al., "Optofluidic devices and applications in photonics, sensing and imaging." Lab on a Chip 12.19 (2012): 3543-3551.
Persichetti et al., "Multifunctional optofluidic lab-on-chip platform for Raman and fluorescence spectroscopic microfluidic analysis." Lab on a Chip 17.15 (2017): 2631-2639.
Sapra et al., "Inverse design and demonstration of broadband grating couplers." IEEE Journal of Selected Topics in Quantum Electronics 25.3 (2019): 1-7.
Segev et al., "Patterned photostimulation via visible-wavelength photonic probes for deep brain optogenetics." Neurophotonics 4.1 (2016): 011002. 16 pages.
Shen et al., "Ultra-high-efficiency metamaterial polarizer." Optica 1.5 (2014): 356-360.
Takehara et al., "On-chip cell analysis platform: Implementation of contact fluorescence microscopy in microfluidic chips." Aip Advances 7.9 (2017): 095213. 9 pages.
Weller-Brophy et al., "Waveguide diffraction gratings in integrated optics." Integrated Optical Circuit Engineering II. vol. 578. International Society for Optics and Photonics, 1985. 6 pages.
Wuytens et al., "On-chip surface-enhanced Raman spectroscopy using nanosphere-lithography patterned antennas on silicon nitride waveguides." Optics Express 25.11 (2017): 12926-12934.

Chen et al., "All-optical photoacoustic microscopy." Photoacoustics 3.4 (2015): 143-150.
Dangi et al., "Dynamics of strongly coupled fluid-filled microcavities and PMUTs in integrated microfluidic devices." International Design Engineering Technical Conferences and Computers and Information in Engineering Conference. vol. 50145. American Society of Mechanical Engineers, 2016. 7 pages.
Dhakal et al., "Silicon-nitride waveguides for on-chip Raman spectroscopy." Optical Sensing and Detection III. vol. 9141. International Society for Optics and Photonics, 2014. 8 pages.
Graydon, "On-chip spectroscopy." Nature Photonics 12.4 (2018): 189-189.
Huang, "Stress effects on the performance of optical waveguides." International Journal of Solids and Structures 40.7 (2003): 1615-1632.
Kerman et al., "Integrated nanophotonic excitation and detection of fluorescent microparticles." ACS Photonics 4.8 (2017): 1937-1944.
Kim et al., "Air-coupled ultrasound detection using capillary-based optical ring resonators." Scientific reports 7.1 (2017): 1-11.
Li et al., "A transparent broadband ultrasonic detector based on an optical micro-ring resonator for photoacoustic microscopy." Scientific reports 4.1 (2014): 1-8.
Maxwell et al., "Polymer microring resonators for high-frequency ultrasound detection and imaging." IEEE Journal of Selected Topics in Quantum Electronics 14.1 (2008): 191-197.
Michaels et al., "Inverse design of near unity efficiency perfectly vertical grating couplers." Optics express 26.4 (2018): 4766-4779.
Offrein et al., "A very short planar silica spot-size converter using a nonperiodic segmented waveguide." Journal of Lightwave Technology 16.9 (1998): 1680. 6 pages.
Ouyang et al., "Integrated photonics interferometric interrogator for a ring-resonator ultrasound sensor." Optics Express 27.16 (2019): 23408-23421.
Peyskens et al., "Waveguide excitation and collection of surface-enhanced Raman scattering from a single plasmonic antenna." Nanophotonics 7.7 (2018): 1299-1306.
Schriever et al., "Strained silicon photonics." Materials 5.5 (2012): 889-908.
Singh et al., "Chemical characterization of aerosol particles using on-chip photonic cavity enhanced spectroscopy." ACS sensors 4.3 (2019): 571-577.
Singh et al., "Inverse design of photonic metasurface gratings for beam collimation in opto-fluidic sensing." arXiv preprint arXiv:1911. 08957 (2019). 10 pages.
Singh et al., "On-chip photonic particle sensor." Microfluidics, BioMEMS, and Medical Microsystems XVI. vol. 10491. International Society for Optics and Photonics, 2018. 7 pages.
Singh et al., "Towards on-chip mid infrared photonic aerosol spectroscopy." Applied Physics Letters 113.23 (2018): 231107. 5 pages.
Singh, Whispering photons: on-chip biophotonic integrated circuits for point-of-care diagnostics. Diss. Massachusetts Institute of Technology, 2018. 121 pages.
Tamir et al., "Analysis and design of grating couplers." Applied physics 14.3 (1977): 235-254.
Wang et al., "A practical guide to photoacoustic tomography in the life sciences." Nature methods 13.8 (2016): 627-638.
Westerveld et al., "Micro-Opto-Mechanical Pressure, Sound, and Ultrasound Sensors in Silicon-Nitride Photonic Technology." 2019. 3 pages.
Westerveld, "Silicon photonic micro-ring resonators to sense strain and ultrasound." (2014). 219 pages.
Wissmeyer et al., "Looking at sound: optoacoustics with all-optical ultrasound detection." Light: Science & Applications 7.1 (2018): 1-16.
Yakar et al., "Energy Efficiency of Microring Resonator (MRR)-Based Binary Decision Diagram (BDD) Circuits." 2019 IEEE International Conference on Rebooting Computing (ICRC). IEEE, 2019. 8 pages.

(56) References Cited

OTHER PUBLICATIONS

Zhang et al., "A miniature all-optical photoacoustic imaging probe." Photons plus ultrasound: imaging and sensing 2011. vol. 7899. SPIE, 2011. 7 pages.

* cited by examiner

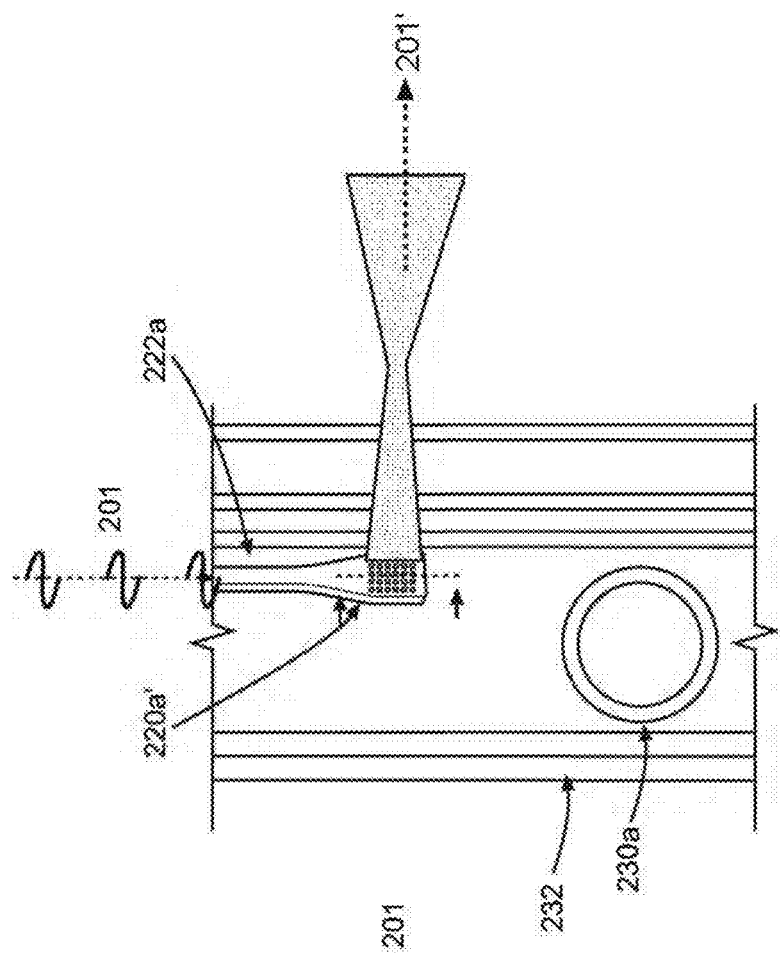
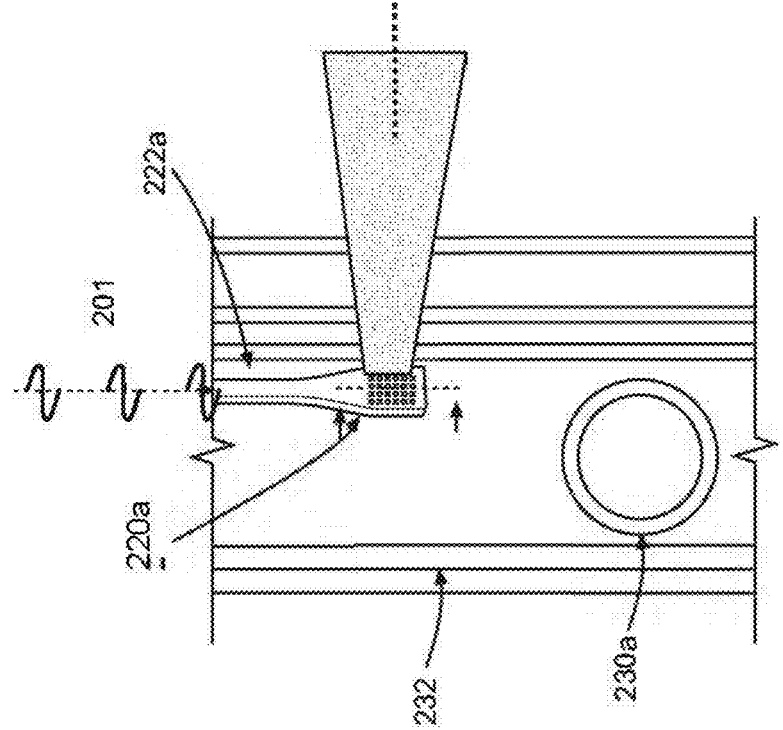

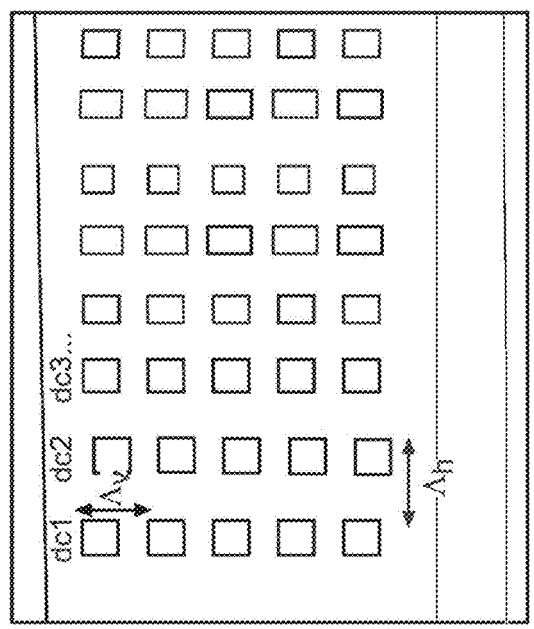
FIG. 3B
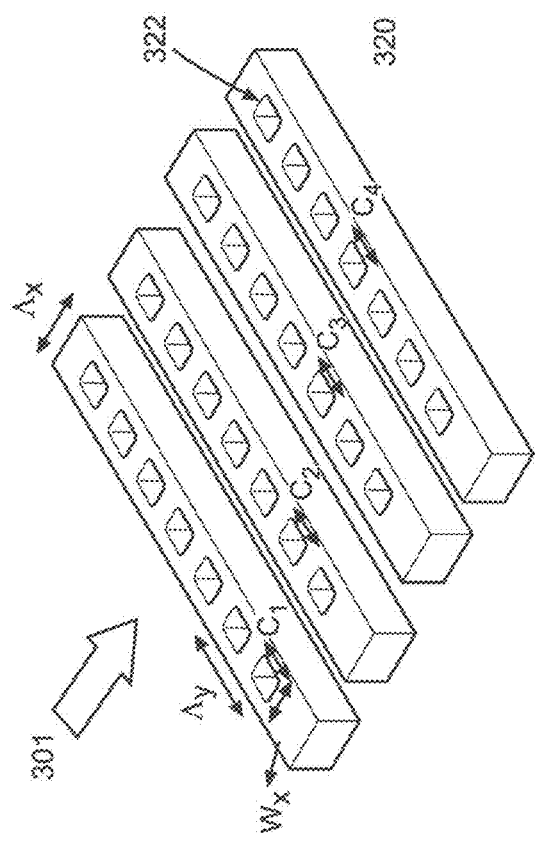
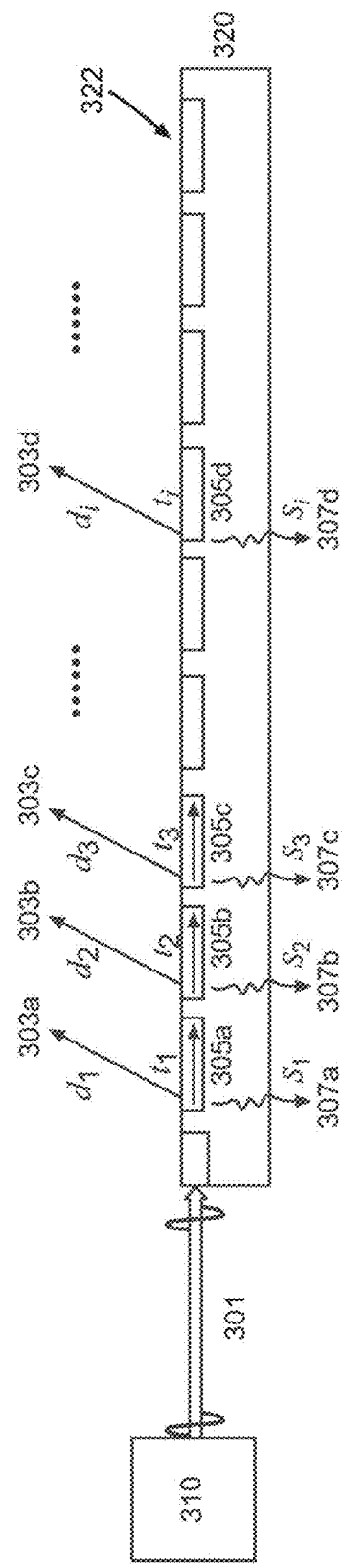
FIG. 3C

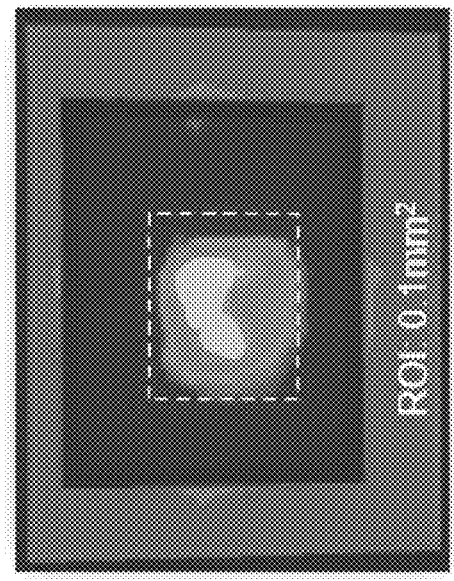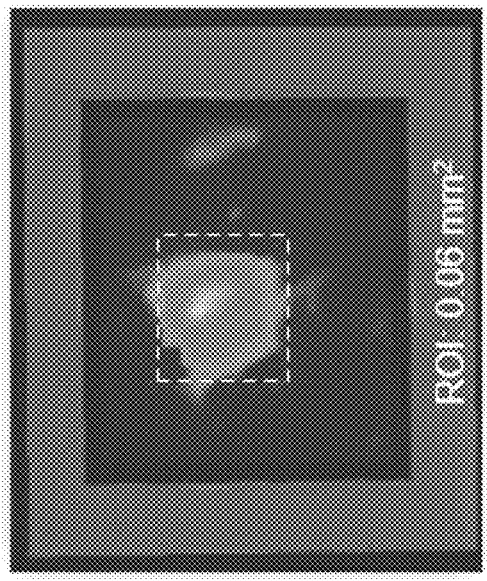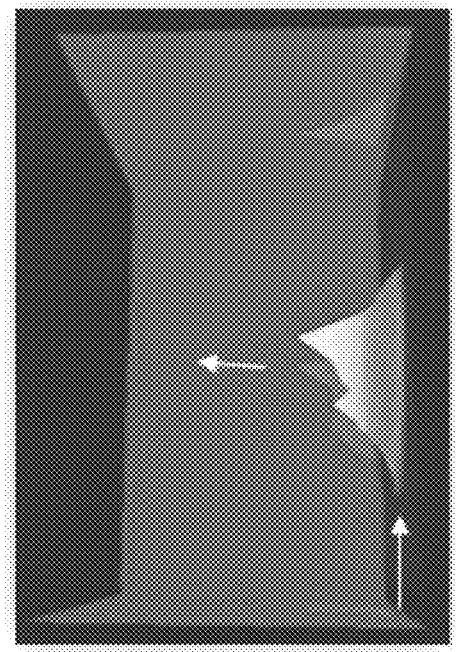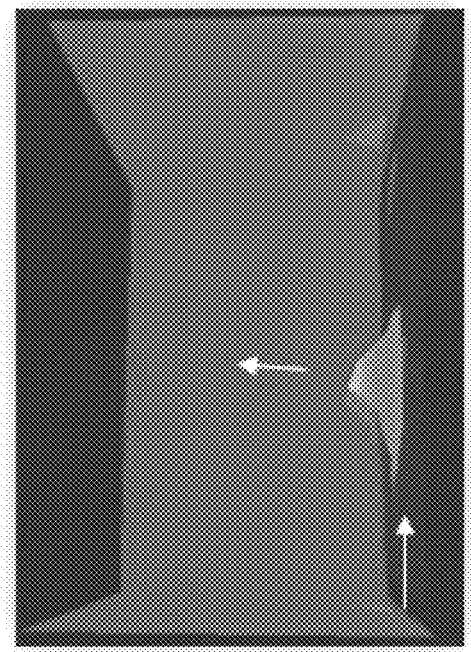

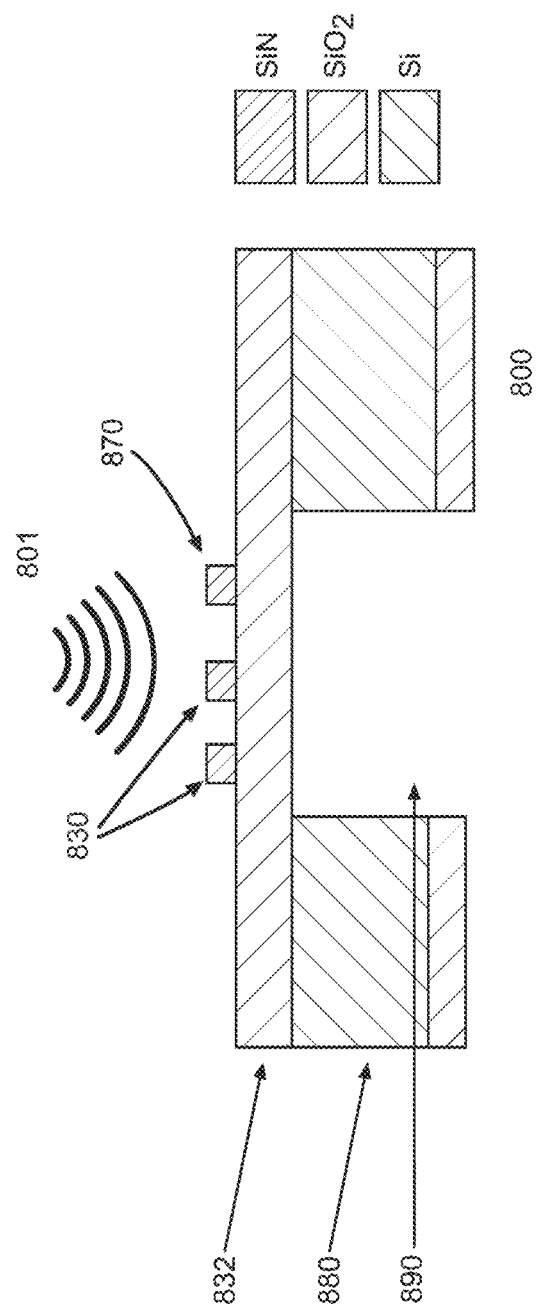

MICROSCALE PHOTOACOUSTIC SPECTROSCOPY, IMAGING, AND MICROSCOPY

CROSS-REFERENCE TO RELATED APPLICATION(S)

This application claims the priority benefit, under 35 U.S.C. § 119(e), of U.S. application Ser. No. 62/858,351, filed on Jun. 7, 2019, which is incorporated herein by reference in its entirety.

BACKGROUND

Photoacoustic imaging (PAI) has attracted much attention over the past two decades for various biomedical applications. PAI is a hybrid imaging modality that synergizes the acoustic and optical domains to generate enhanced images. In PAI, a nonlinear interaction between light and biological tissue causes the biological tissue to emit ultrasound waves generated by biological tissue in response to incident light. These ultrasound waves can be detected and used to generate an image of the biological tissue. PAI can provide functional and metabolic activity information through endogenous and exogenous imaging contrast. PAI can also offer much higher penetration depths than optical imaging techniques because the acoustic scattering mean free path is orders of magnitude longer than the optical scattering mean free path.

Common PAI instrumentation uses medical ultrasound imaging transducer technology. However, the generated ultrasound signal in PAI can vary significantly in comparison to conventional ultrasound imaging. Ultrasound imaging uses narrowband signals and transducers for ultrasound imaging operate with narrow bandwidths. A conventional ultrasound imaging system typically uses a bandwidth that is about of its operating bandwidth, e.g., about 2 MHz within an 8-12 MHz operational range. In contrast, photoacoustic signals generated from biological tissue can be broadband signals spanning from sub MHz to hundreds of MHz. In addition, photoacoustic signals generated from the biological endogenous tissues are almost three orders of magnitude weaker than those signals generated by medical ultrasound imaging. There is a desire for PAI transducers than can collect signals over a broad band with a high level of sensitivity. There is also a desire for PAI transducers that can collect ultrasound signals over a wide angle of acceptance. A PAI transducer with these qualities may improve the field of view and resolution for image reconstruction.

SUMMARY

The present technology addresses the desires for PAI that operates over a broad bandwidth with high sensitivity and a wide angle of acceptance. This technology can be implemented as a miniaturized on-chip PAI device with optical and acoustic modules integrated together. Silicon photonics enables flexible, low-cost, and scalable approaches for the miniaturization of integrated electronic and photonic systems, enabling on-chip PAI for medicine and biology.

Embodiments of the present technology include a sensor. The sensor includes an excitation light source, an output coupler, a first resonator, at least one probe light source, at least one detector, and a processor. In operation, the excitation light source emits an excitation beam. The output coupler, which is in optical communication with the excitation beam, couples the excitation beam into an analyte medium, and the excitation beam causes the analyte medium to emit a photoacoustic wave. The first resonator, which is in acoustic communication with the analyte medium, has a first resonance frequency that shifts in response to the photoacoustic wave. At least one probe light source, which is in optical communication with the first resonator, couples a first probe beam into the first resonator. At least one detector, which is in optical communication with the first resonator, detects at least a portion of the first probe beam transmitted or reflected by the first resonator. The processor, which is operably coupled to the at least one detector, determines a shift of the first resonance frequency in response to the photoacoustic wave based on at least a portion of the first probe beam detected by the detector.

The sensor may include a collimator to collimate the excitation beam. The collimator may include a meta-surface. The photoacoustic wave may have at least one spectral component in a band from about 1 MHz to about 50 MHz. The photoacoustic wave may have at least one spectral component in a band from about 1 MHz to about 20 MHz. The first resonator may be disposed on a flexible membrane configured to deflect in response to the photoacoustic wave. The first resonator may include a polymer ring resonator.

The sensor may additionally include a second resonator. The second resonator, in acoustic communication with the analyte medium and in optical communication with at least one probe light source and at least one detector, may have a second resonance frequency that shifts in response to the photoacoustic wave. The second resonance frequency may be different than the first resonance frequency. At least one probe light source may be configured to couple a second probe beam into the second resonator. At least one detector may be configured to detect at least a portion of the second probe beam transmitted or reflected by the second resonator. The processor may be configured to determine a shift of the second resonance frequency in response to the photoacoustic wave based on at least a portion of the second probe beam detected by the detector. The processor may be configured to determine a temporal shift between the shift in the first resonance frequency and the shift in the second resonance frequency. The first resonator may be disposed on a membrane that vibrates in response to the photoacoustic wave.

The sensor may further include a microfluidic channel. The microfluidic channel, in optical communication with the output coupler and the first resonator, may flow the analyte medium past the output coupler and the first resonator.

Another embodiment of the present technology includes a neurophotonic probe. The neurophotonic probe includes a substrate, probe ring resonators, at least one input waveguide, and at least one output waveguide. The substrate of the neurophotonic probe has a tip for penetrating neural tissue. In operation, the probe ring resonators, which are disposed along the tip of the substrate, have respective resonance frequencies that shift in response to acoustic excitation. At least one input waveguide, which is disposed on the substrate and evanescently coupled to the probe ring resonators, couples probe light into the ring resonators. At least one output waveguide, which is disposed on the substrate and evanescently coupled to the probe ring resonators, couples probe light out of the probe ring resonators.

At least a portion of the tip of the substrate may be configured to deflect in response to the acoustic excitation, thereby shifting the respective resonance frequencies of the probe ring resonators. The neurophotonic probe may further include wavelength-division multiplexing (WDM) ring resonators. The WDM ring resonators may be evanescently coupled to at least one output waveguide and a bus waveguide and may couple the probe light from at least one output waveguide to the bus waveguide.

Another embodiment of the present technology includes a method of imaging neural tissue. The method includes inserting a neural probe into the neural tissue, measuring a shift in a resonance frequency of a first optical ring resonator on the neural probe caused by a photoacoustic excitation propagating through the neural tissue, and generating an image of the neural tissue based at least in part on the shift in resonance frequency of the first optical ring resonator.

Generating the image may include generating the image with a spatial resolution of about 20 microns to about 50 microns. Generating the image may include generating the image over a volume of about 1 cubic millimeter. The method may additionally include measuring a shift in a resonance frequency of a second optical ring resonator on the neural probe caused by the photoacoustic excitation propagating through the neural tissue. The method may additionally include illuminating the neural tissue with a probe beam to produce the photoacoustic excitation propagating through the neural tissue.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally and/or structurally similar elements).

FIG. 2C is a closer view of a collimator and resonator on the neurophotonic microscale photoacoustic imaging sensor probes of FIGS. 2A and 2B, where the collimator is designed for acoustic resolution.

FIG. 2D is a closer view of a collimator and resonator on the neurophotonic microscale photoacoustic imaging sensor probes of FIGS. 2A and 2B, where the collimator is designed for optical resolution.

FIG. 3B is a diagram depicting dimensions of the photonic waveguide-based metasurface collimator of FIG. 3A.

FIG. 3C is a diagram depicting another view of the waveguide-based metasurface collimator of FIG. 3A.

FIG. 7A shows a side view of an experimentally measured emission from a waveguide-based metasurface collimator at 1× magnification.

FIG. 7B shows a top view of the experimentally measured emission from the waveguide-based metasurface collimator at 1× magnification in FIG. 7A.

FIG. 7C shows a side view of an experimentally measured emission from a conventional binary grating at 1.5× magnification.

FIG. 7D shows a top view of the experimentally measured emission from the waveguide-based metasurface collimator at 1.5× magnification in FIG. 7C.

FIG. 8 is a cross-sectional diagram of an on-chip photoacoustic transducer.

DETAILED DESCRIPTION

Miniature Photoacoustic Sensor

A miniature, on-chip, platform for both excitation and detection may offer several advantages. First, the field-of-view for imaging may be scaled up by multiplexing a large number of excitation sources. Second, a miniature platform may provide a compact hardware geometry to implement solutions at a low-cost with high volume production. Third, a miniature platform may enable biological analysis, such as cell screening, probing, and automation.

Figure 1A:
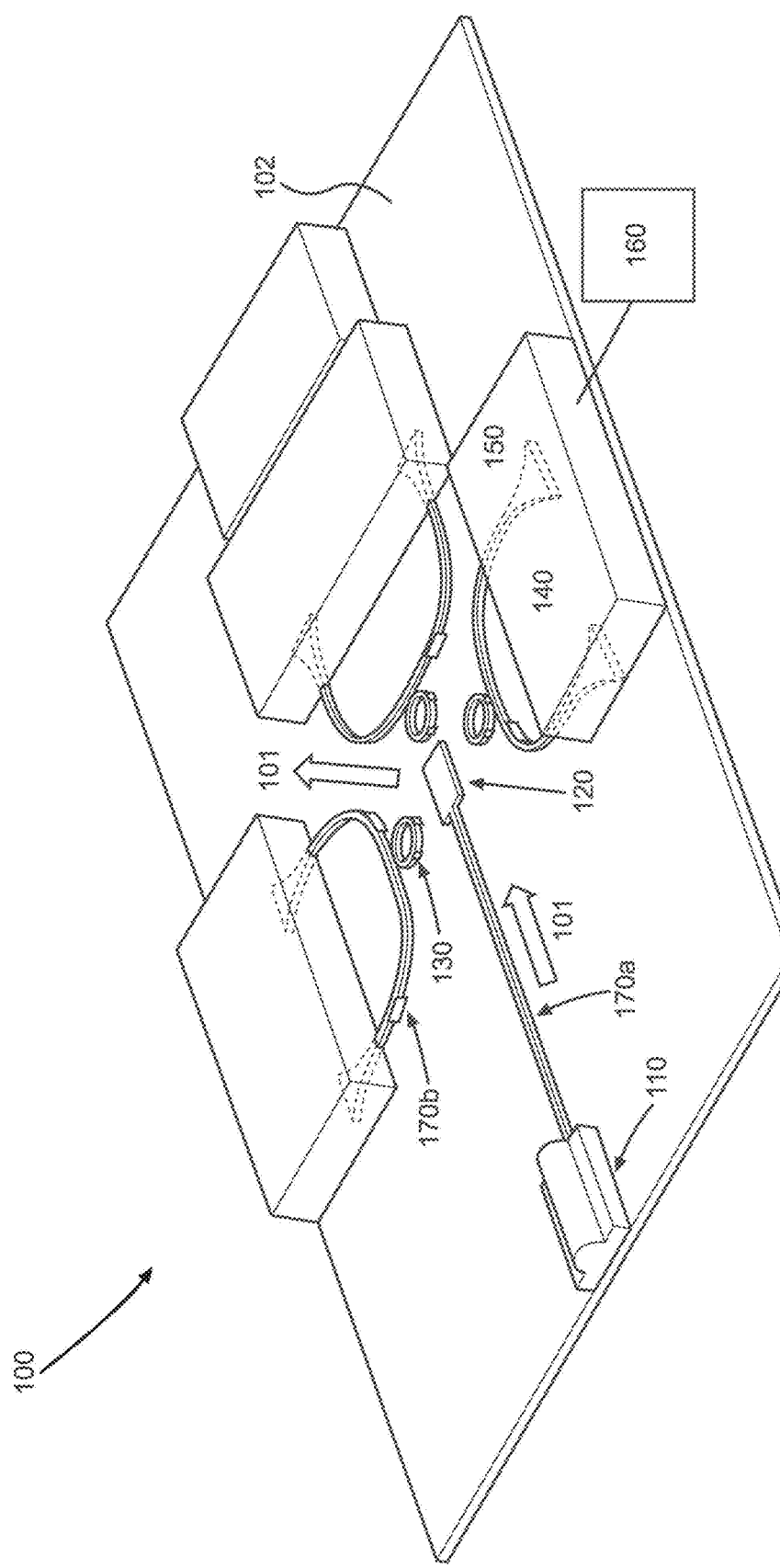
FIG. 1A is a diagram of a microscale photoacoustic sensor.
Figure 1B:
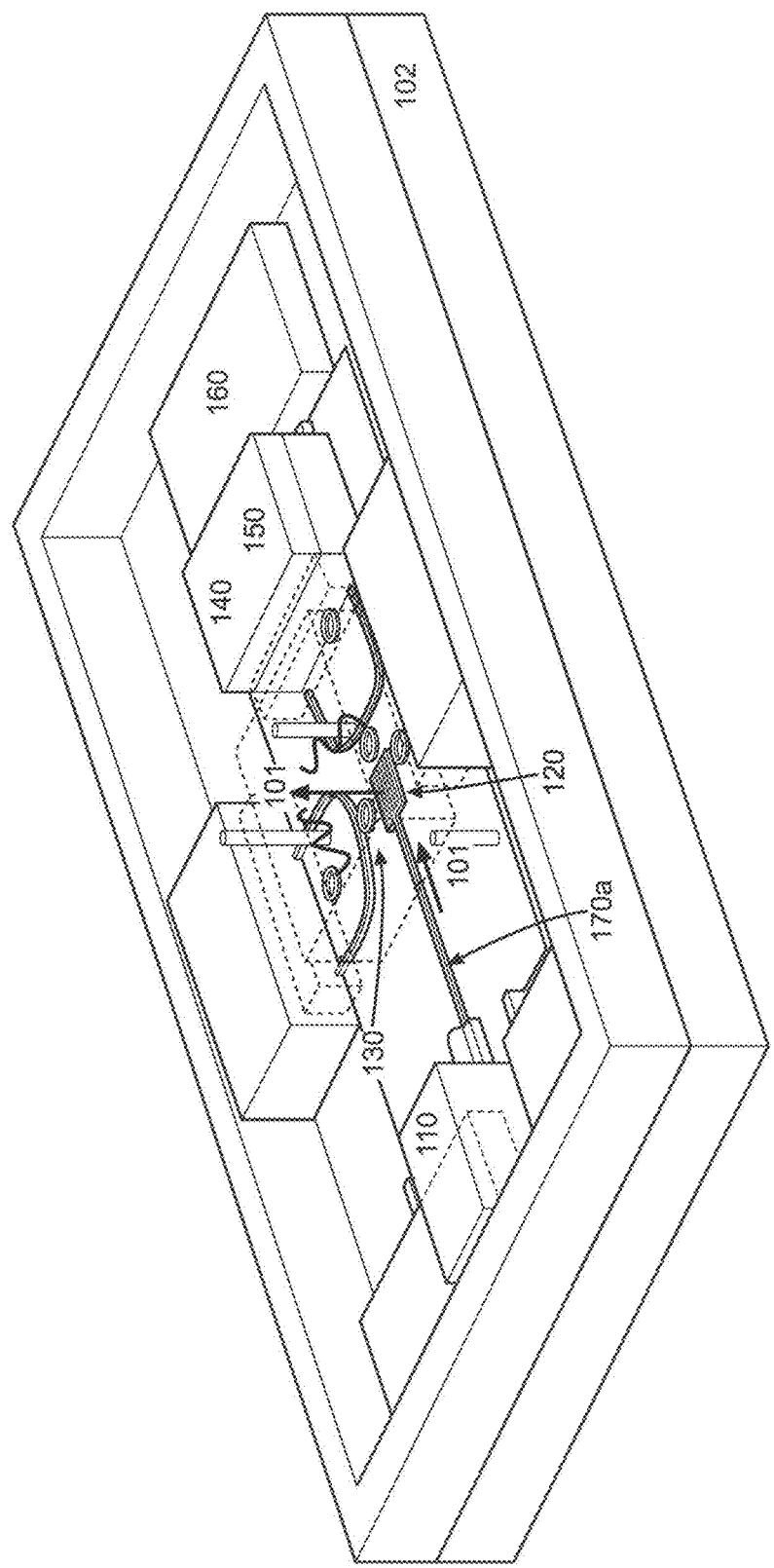
FIG. 1B is another view of the microscale photoacoustic sensor of FIG. 1A.

FIGS. 1A and 1B show different views of a microscale photoacoustic sensor 100 with integrated photonic components for stimulating and detecting photoacoustic emissions from biological tissue and other matter. This microscale photoacoustic sensor 100 can be used for spectroscopy, imaging, or microscopy.

The sensor 100 includes a coherent excitation light source 110 (e.g., a laser), an output coupler 120, and a waveguide 170a that couples the excitation light source 110 and the output coupler 120. The excitation light source 110, output coupler 120, and waveguide 170a may all be fabricated on a flexible substrate or membrane 102. The excitation light source 110 emits an excitation beam 101, which is guided by the waveguide 170a to the output coupler 120. The output coupler 120 couples the excitation beam 101 into an analyte medium that is deposited on or flows over the membrane 102. The output coupler 120 may be a collimator or a binary grating surface, which diffracts light out of the plane of the sensor. The sensor 100 also includes at least one resonator 130, probe light source 140, and waveguide 170b fabricated on the membrane 102. The waveguide 170b is evanescently coupled to the resonator 130, which may be a ring resonator or an unbalanced Mach Zehnder interferometer, and connects the probe light source 140 to a detector 150, which in turn is coupled to a processor 160.

The membrane 102 is a flexible substrate with some elasticity and free boundary conditions. It may be modelled using a spring-mass-damper system with a characteristic resonance. The characteristics of the membrane 102 are its quality factor and center frequency and bandwidth of its resonance peak. A lower quality factor produces a broader bandwidth. These characteristics may be designed so that the membrane 102 vibrates with a certain central frequency and a certain bandwidth. For example, the membrane 102 may vibrate at a 1 MHz central frequency and a 50% bandwidth.

In operation, the light source 110 launches the excitation beam 101 into the waveguide 170a. The output coupler 120 couples the excitation beam 101 out of the waveguide 170a and into the analyte medium. Depending on the coupler's configuration, the coupler 120 may collimate the excitation beam 101 or focus it to a point within or beyond the analyte medium. The excitation beam 101 interacts nonlinearly with analyte medium to produce a photoacoustic wave 105, which propagates through the analyte medium back towards the sensor 100. The photoacoustic wave 105 causes the membrane 102 to deflect or vibrate. This deflection or vibration deforms the resonator 130, shifting its resonance frequency.

A probe beam from the probe light source 140 probes the resonant frequency of the resonator 130 via the waveguide 170b. If the wavelength of the probe beam matches the resonator's resonant frequency, the probe beam is at least partially coupled from the waveguide 170b into the resonator 130, where it remains until it is coupled out of the resonator 130 (neglecting absorption). This causes the signal sensed by the detector 150 to fluctuate as a function of the (mis)match between the probe beam wavelength and the resonator's resonance frequency. The processor 160 coupled to the detector 150 can quantify the shift in the resonator's resonance frequency based on the intensity of the probe light detected by the detector 150.

For instance, if the wavelength of the probe beam matches the resonance frequency of the unperturbed resonator 130, then the detector 150 should not detect any light when the resonator is in an unperturbed state. Instead, it should detect light when the resonator 130 is perturbed. Similarly, if the wavelength of the probe beam does not match the resonance frequency of the unperturbed resonator 130, then the detector 150 should detect light unless the resonator is perturbed enough to shift its resonance frequency to overlap in wavelength/frequency with the probe beam. The probe beam's wavelength can also be chirped or swept (e.g., with a tunable laser) so that it probes different possible resonance frequencies at different moments in time in a repeatable fashion. By sensing when the detected intensity dips, the processor 160 can match the time bin to the probe beam wavelength/ frequency that matches the resonator's instantaneous resonance frequency. This makes it possible to both detect and quantify the resonator's instantaneous resonance frequency.

The processor 160 matches the detected resonance frequency (shift) to the photoacoustic wave that caused the resonance frequency shift. The resonators 130 are in different positions on the sensor and so detect photoacoustic waves from different angles, just like pixels in a photodetector array. If the resonators 130 are ring resonators, they can be driven in a phase-locked loop, with the frequency of the probing beam frozen and the detector 150 and processor 160 measuring the change in intensity of the probing mean. The detector 150 and processor 160 can measure time-domain changes in the intensity output from the ring resonators, thereby giving information on changes in the photoacoustic wave's phase. In addition to measuring changes in the photoacoustic wave's phase, the processor 160 may measure changes in the photoacoustic wave's amplitude using vector analysis. If the resonators 130 are Mach Zehnder Interferometers (MZI), changes in intensity in the time domain can be measured at the detector 150, thereby giving information on changes in the photoacoustic wave's phase.

Figure 1C:
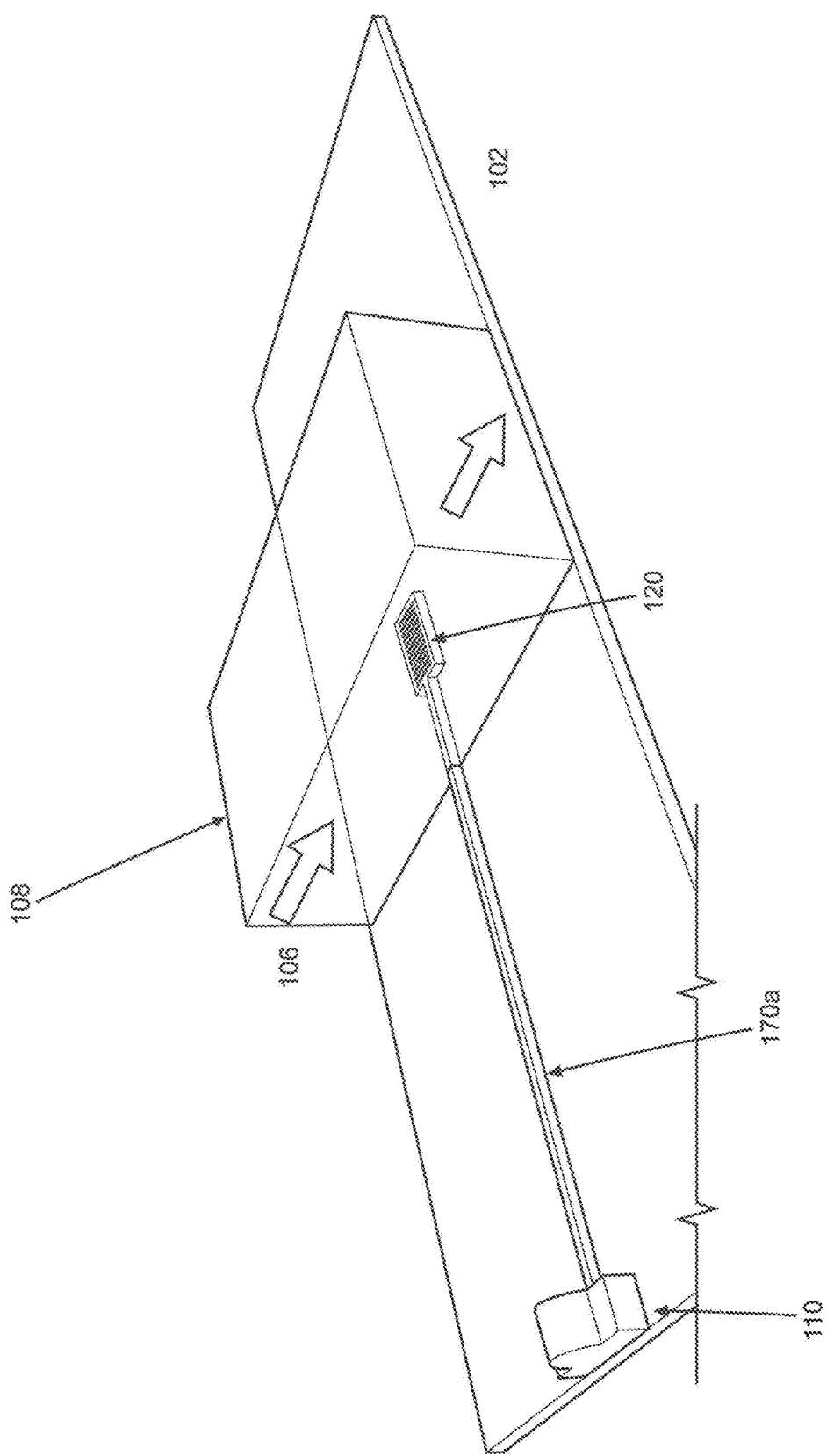
FIG. 1C is a diagram of a miniature photoacoustic sensor within a microfluidic channel.

FIG. 1C illustrates how the microscale photoacoustic sensor 100 may be used in a microfluidic application. An integrated microfluidic channel 108 is laid over the output coupler 120 so that the excitation beam 101 emitted by the output coupler 120 passes through a fluid analyte medium 106 that flows through the channel 108. The membrane 102 that supports the resonator(s) 130 is in acoustic communication with the fluid analyte medium 106. For example, the fluid analyte medium 106 may flow through the channel 108 over at least a portion of the membrane 102 (though not necessarily the portion that supports the resonator(s) 130). In any event, the liquid analyte medium 106 flows through the path of the excitation beam 101 emitted by the output coupler 120. The excitation beam 101 causes the fluid analyte medium 106 to emit a photoacoustic wave 105, which in turn moves or shakes the membrane 102. In turn, this movement of the membrane 102 by the photoacoustic wave 105 may shift the resonance frequency of the resonator 130.

Figure 2A:
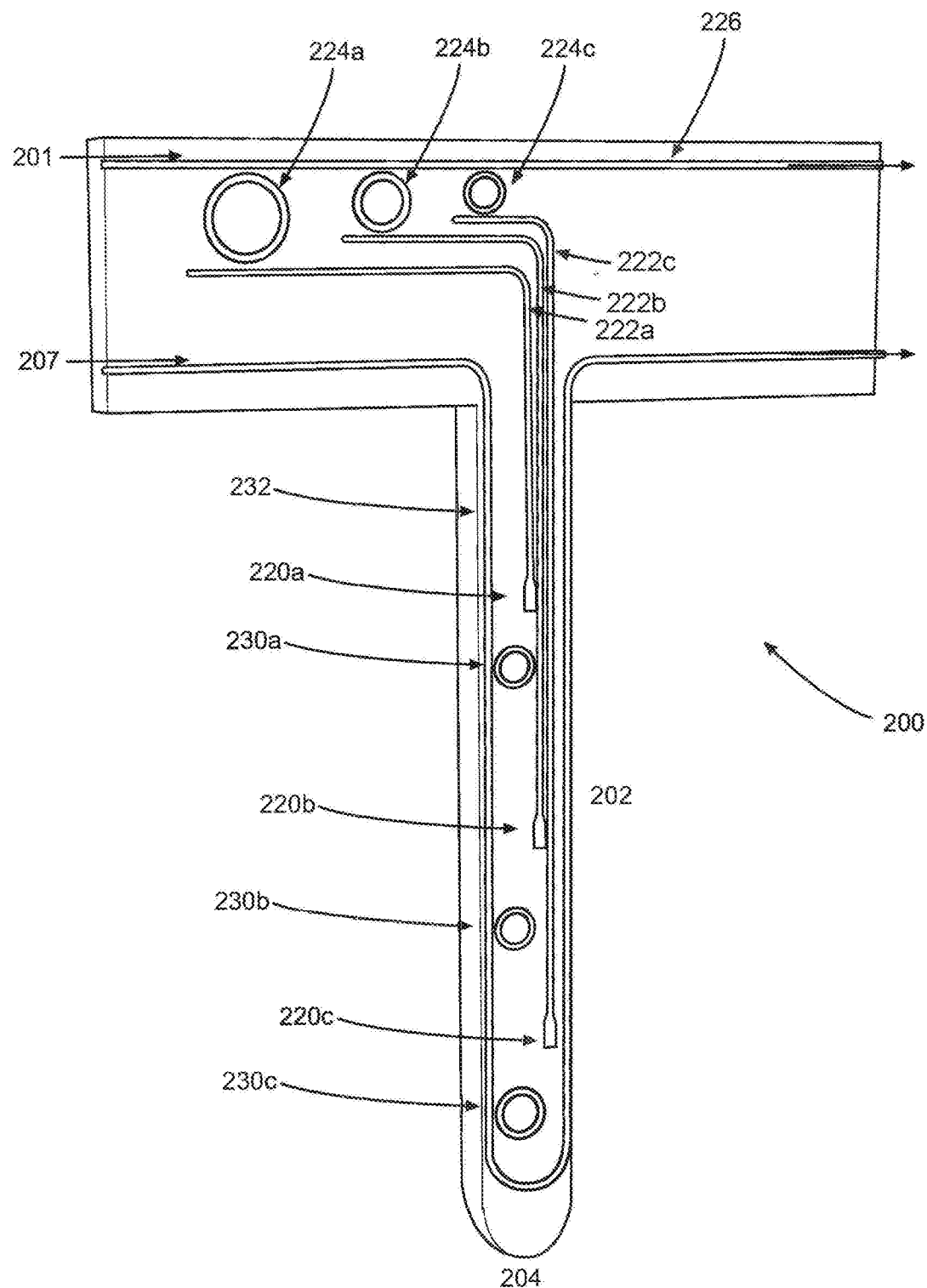
FIG. 2A is diagram of a probe in a neurophotonic microscale photoacoustic imaging sensor.

FIGS. 2A-2D illustrate a microscale photoacoustic sensor 200 suitable for photoacoustic imaging of neural tissue 205 or other biological tissue. FIG. 2A shows the sensor's probe 202, which has a tip 204 that is sharp enough to penetrate the tissue 205 without damaging it. The probe 202 supports three output couplers 220a, 220b, and 220c, which are coupled to respective waveguides 222c, 222b, and 222c. These waveguides 222a, 222b, and 222c are coupled to an excitation bus waveguide 226 via respective ring resonators 224a, 224b, and 224c. The probe 202 also supports ring resonators 230a, 230b, and 230c, which are evanescently coupled to a probe bus waveguide 232. The portion of the probe 202 that supports the ring resonators 230 is flexible enough to bend or deflect in response to a photoacoustic wave propagating through the tissue 205.

The resolution of the microscale photoacoustic sensor 200 scales with the number of ring resonators. With a higher number of ring resonators, the microscale photoacoustic sensor has a higher resolution in measuring the temporal shift in the photoacoustic wave. Likewise, with a higher number of ring resonators on the microscale photoacoustic sensor 200, the image derived from the temporal shift information has better resolution and fewer reconstruction artifacts. As an example, a probe 202 that is about 8 mm to about 10 mm long, 300 μm wide, and about 5 μm to about 10 μm thick can have about 32 to about 128 ring resonators on its surface.

The tip 204 may be coated with a bio-compatible material. For example, the tip 204 may be coated with PDMS or parylene. The tip 204 may be inserted up to about 1 cm into biological tissue. The bio-compatible coating has a Young's modulus within about 1 MPa of the Young's modulus of the neural or biological tissue penetrated. The similar Young's modulus may help to decrease any mechanical stress or immune response in the tissue when the microscale photoacoustic sensor 200 is inserted.

Like the sensor 100 in FIGS. 1A-1C, the sensor 200 in FIGS. 2A-2D operates by illuminating the tissue with a pump or excitation beam 201 that generates a photoacoustic wave, which the sensor 200 detects and uses to generate a photoacoustic image of the tissue 205. More specifically, an excitation light source (not shown) generates the excitation beam 201, which is coupled into the tissue via the output collimators 220, excitation bus waveguide 226, ring resonators 224, and waveguides 222. The ring resonators 224 may have equal radii, to couple light 201 of the same wavelength to their respective output couplers 220, or different radii, to couple light 201 of different wavelengths to the different output couplers 220. This enables the probe 200 to illuminate the tissue with light 201 at different wavelengths. This light generates one or more photoacoustic waves 203 that propagate within the tissue 205. Wavelength-division multiplexing (WDM) may be used to channel light 201 of different wavelengths into different output couplers 220 for multispectral photoacoustic imaging. WDM can be used to identify the source of the excitation light 201 when deriving an image from the photoacoustic signal.

The microscale photoacoustic sensor's ring resonators 230 sense the photoacoustic waves 203. Each ring resonator 230 has a resonance frequency that shifts in response to movement of the corresponding probe 202 by the photoacoustic waves 203. The ring resonators 230 may have the same resonance frequency or different resonance frequencies. If the ring resonators 230 have different resonant frequencies, and those resonant frequencies are separated by more than the expected frequency shifts, then the resonant frequencies can be uniquely mapped to the ring resonators 230. In other words, the resonance frequencies can be spectrally multiplexed, making it possible to interrogate all of them using a single probe beam 207 from a tunable probe light source (not shown) swept over a range that spans the range of the resonance frequencies. Each ring resonator 230 reflects and/or transmits a portion of the probe beam 203. The probe waveguide 232 guides the transmitted and reflected portions of the probe beam to a detector (not shown).

Figure 2B:
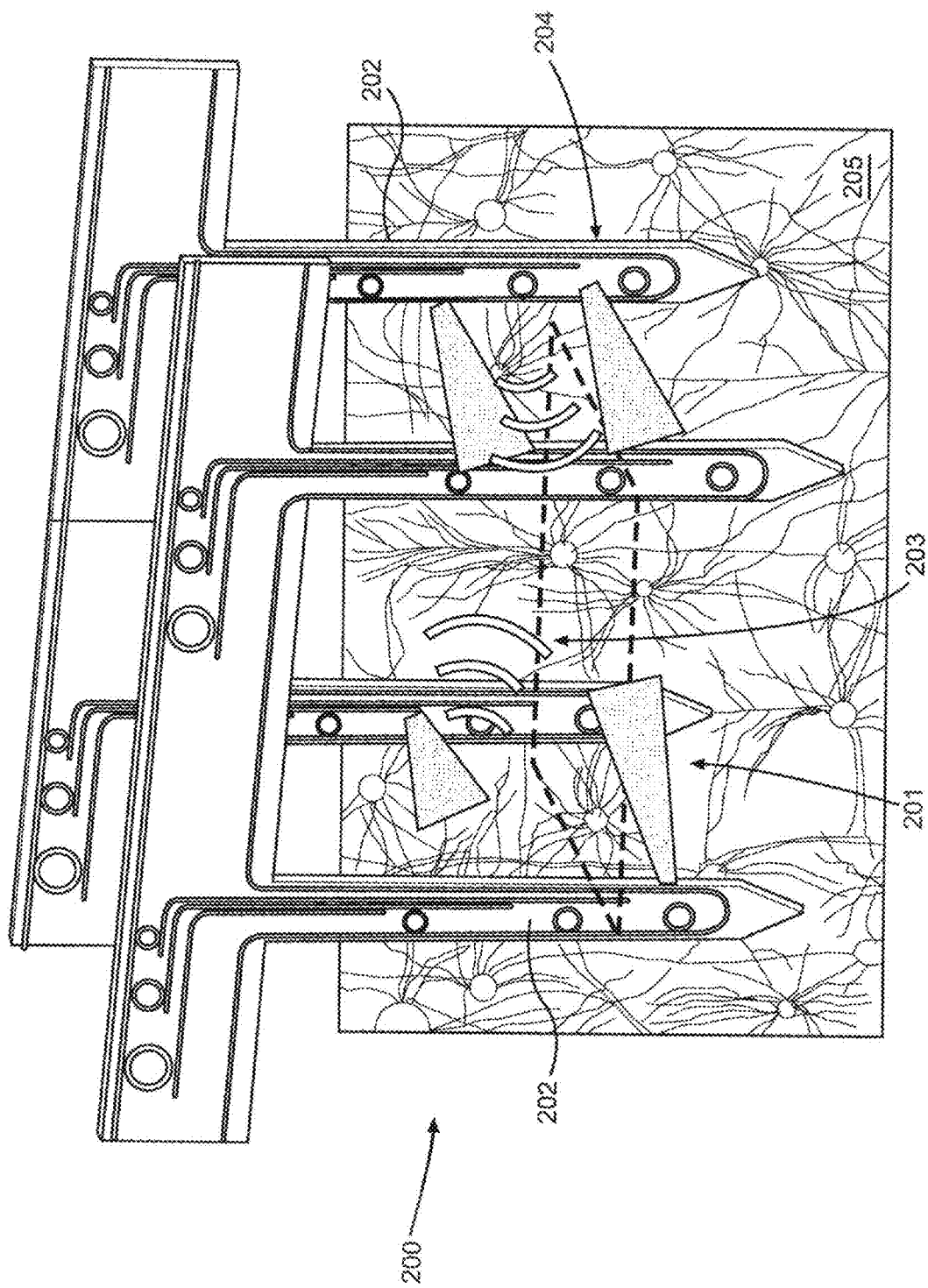
FIG. 2B is a diagram of a neurophotonic microscale photoacoustic imaging sensor with multiple probes for super resolution PAI.

FIG. 2B is an illustration of a microscale photoacoustic sensor 200 with an array of four probes 202 inserted into neural tissue 205. Microscale photoacoustic sensor components (output couplers 220, ring resonators 230, and waveguides) reside on each of the four probes 202. Each probe 202 may emit one or more excitation beams 201 to excite one or more photoacoustic signals 203 within the neural tissue 205. The probes 202 may emit excitation beams 201 sequentially or simultaneously; for instance, each probe 202 may emit excitation beams 201 in turn, with all of the probes 202 "listening" for the corresponding acoustic waves 203. This may make it possible to localize the sources of the acoustic waves 203 for generating a 3D image of the neural tissue 205. In this manner, the microscale photoacoustic sensor 200 with an array of neural-penetrating probes 202 may be used to perform photoacoustic tomography. A microscale photoacoustic sensor with an array of tips may be used to image up to about 10,000 neurons with single-neuron spatial resolution in a 1 $mm^3$ sampling volume of neural tissue 205.

FIGS. 2C and 2D illustrate the tunability of spatial resolution in the microscale photoacoustic sensor 200. As explained above, the output coupler 220, which may be a metasurface lens or collimator as described below, emits probe light 201 into the neural tissue 205. The output coupler 220 may be designed to diffract the excitation beam 201 with a range of different beam shapes and focus parameters. For example, the output coupler 220a may diffract light 201 with a lateral resolution of about 100 μm for acoustic resolution PAI, as shown in FIG. 2C. As another example, FIG. 2D shows a modified output coupler 220' that diffracts light 201' with a lateral resolution of about 0.22 μm for optical resolution PAI. Optical resolution results in a smaller field of view and higher spatial resolution, whereas acoustic resolution results in a larger field of view and lower spatial resolution.

Acoustic resolution and optical resolution offer different advantages. Acoustic resolution offers better depth penetration and a larger field of view, while also having lower resolution. With acoustic resolution, output couplers 220 and resonators 230 can be placed with less spatial precision. Acoustic resolution is appropriate for measuring photoacoustic waves in larger volumes. In contrast, optical resolution offers higher resolution, lower penetration, and a smaller field of view. With optical resolution, output couplers 220 and resonators 230 may need to be placed with more care. Optical resolution is appropriate for measuring photoacoustic waves with higher resolution within smaller volumes. For example, optical resolution can be used to image individual neural cells.

Photonic Waveguide-Based Metasurface Collimator

Figure 3A:
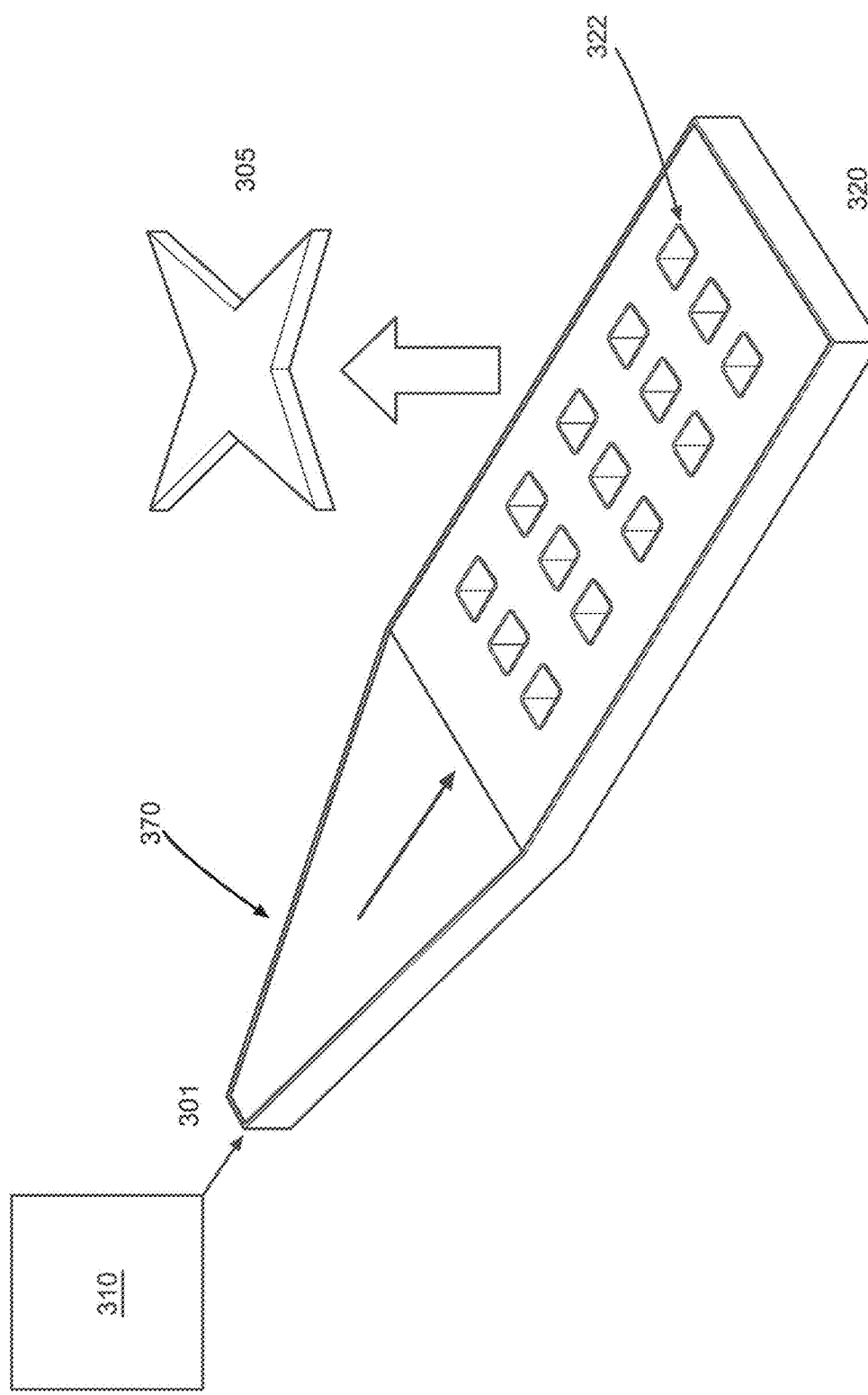
FIG. 3A is a diagram of a photonic waveguide-based metasurface collimator.

FIGS. 3A-3C show different views of a photonic waveguide-based metasurface collimator 320 suitable for use in a photoacoustic sensor. The photonic waveguide 370 terminates in a metasurface collimator structure 320, which has an array of metasurface elements or diffracting grooves 322 with a pitch of about 60 to about 80 μm. Each metasurface element 322 is about 400 nm thick. The metasurface collimator 320 receives a light beam 301 from an excitation light source 310. The light beam 301 propagates through a waveguide 370. The diffracting grooves 322 diffract the light beam out of the plane of the waveguide 370, forming an excitation beam 305 that can cause an analyte medium to emit a photoacoustic wave.

A photonic waveguide-based metasurface collimator 320 may enable the miniaturization of excitation sources and may enable integrated on-chip photon routing and manipulation. A diffracting metasurface collimator 320 can collimate light more uniformly and/or over a wider area than the binary gratings used in conventional out-of-plane couplers. The metasurface collimator 320 may achieve a more uniform emission along the waveguide 370 propagation direction than a binary grating by controlling the amount of energy diffracted from each diffracting groove 322 in proportion to the power loss along the optical path. The power loss may be controlled by designing a unique arrangement of light diffractors 322 along the direction of light propagation.

An inverse modelling approach can be used to design the metasurface grating structure on the photonic waveguide-based metasurface collimator 320 shown in FIGS. 3A-3C. For instance, the collimator can be designed to create a wide collimated beam, which is useful for on-chip optical excitation and detection in bio-sensing applications. Finite difference time domain (FDTD) modeling can be used to design the collimator. The collimator's light diffraction properties are mathematically related to critical design parameters. Rectangular light diffracting grooves 322 in the grating structure on the metasurface collimator can be defined by their duty cycle (C), row period ($\Lambda_y$) along the transverse direction, and line period ($\Lambda_x$) along the propagation direction, as shown in FIG. 3B.

The metasurface collimator 320 may offer a high index region to support orthogonally polarized modes propagating along the axial direction. Assuming the incoming optical wave 301 in the waveguide 370 is of the form $E_0^{inc}(y,z)e^{i(\beta x-\omega t)}$, where $E_0^{inc}(y,z)$ is the amplitude of the electric field and $\beta$ is the propagation constant, the diffracted beam profile is given by, $E_0^{diff}(y,z)e^{i(k_{xn}x-\omega t)}$ with the propagation constant as $$k_{x_n} = \beta_n + i\alpha = \beta_0 + \frac{2n\pi}{\Lambda_x} + i\alpha$$

Here, $\beta_n$ is the propagation constant of the diffracted beam that depends on the periodicity of diffracting grooves 322 in the x direction, $\alpha$ is the energy leakage factor and n is the diffraction order. The angle of diffraction measured from the vertical axis, for nth order of diffraction is given by $$\phi_n = \sin^{-1}\left(\frac{\beta_n}{k_0}\right)$$

Specifically, for out-of-plane diffraction of the beam without any higher-order diffraction, it is customary to satisfy the following conditions, $$\left|n_{wg} - \left(\frac{\lambda}{\Lambda_x}\right)\right| \leq \sqrt{\varepsilon_a} = 1, \, 2\left(\frac{\lambda}{\Lambda_x}\right) - n_{wg} > \sqrt{\varepsilon_{SiO_2}}$$

where $n_{wg}$ is the effective index of the waveguide and $\varepsilon_a$ is the permittivity of the cladding. The cladding may be air or a liquid surrounding the sensor. If the microscale photoacoustic sensor is used as an opto-fluidic integrated sensor, the permittivity of air is replaced by a permittivity value of a surrounding liquid.

The leakage energy in the diffracted beam is given by, $$\alpha = \alpha_h(\omega, D, ff)(\varepsilon_{wg} - \varepsilon_a)^2 \sin^2(\pi \times ff)$$

Here, $\alpha_h(\omega, D, ff)$ is a coefficient that is a strong function of light wave frequency ($\omega$) and of the etch depth (D) and fill factor (ff) of the diffraction grooves. $\varepsilon_{wg}$ and $\varepsilon_a$ are the permittivities of the waveguide and air, respectively. The parameters that control light diffraction are row and line period (in the y- and x-direction respectively) ($\Lambda_y$, $\zeta_x$) and duty cycles (C) of the diffraction grooves. Line period ($\Lambda_x$) controls the angle of diffraction, $\phi_1$, line period ($\Lambda_y$) and duty cycles modulate the effective permittivity of the individual row.

As an example, the width, w, and length, l of the metasurface collimator were maintained at 10 μm and 20 μm, respectively. The center wavelength of the excitation light beam 301 was set to be in the C-band (1550 nm). The metasurface collimator 320 can operate over a wide (~70 nm) range of wavelengths depending on its structure.

Tuning the metasurface collimator 320 for a certain set of conditions is performed in two steps. The first step initializes the duty cycle of an individual row in the metasurface collimator and then performs an iterative gradient descent inverse optimization to collimate the excitation beam 305. The gradient descent method has many advantages, such as enabling the tuning of the metasurface collimator with relatively large degrees of freedom as compared to other gradient-free tuning schemes. Further, the gradient descent method requires fewer simulation steps and does not rely on parametric sweeps or random mathematical perturbations to find optimum values.

The gradient descent method may initialize parameters with relevant values, given the method's sensitivity to initial conditions. To find initial values, an effective mirror model was used for the metasurface collimator. The diffracting grooves 322 can be approximated by the cascaded mirror model to understand light propagation through the structure. FIG. 3C shows the metasurface collimator 320 with its cascade mirror model. Transmission, diffraction, and scattering coefficients of the diffracting groove are assumed as t, d, and s, respectively. Diffraction intensity output from the first diffracting groove is proportional to d, and is given by, $$I_1 = d_1 \quad \text{(i)}$$

Using the cascaded mirror model, we can write intensity $I_2$ and $I_n$ in general, given as, $$I_2 = t_1 d_2 \quad \text{(ii)}$$

$$I_n = t_1 t_2 \ldots t_{n-1} d_n \quad \text{(iii)}$$

The collimated beam requires uniform emission from an individual groove. Mathematically, the condition is represented as, $$I_1 = I_2 = \ldots = I_n = \ldots \quad \text{(iv)}$$

Substituting the equations (i), (ii), (iii) in the condition (iv) results in $$d_1 = t_1 d_2 = t_1 t_2 d_3 = \ldots = t_1 t_2 \ldots t_{n-1} d_n \quad \text{(v)}$$

Assuming $f_i(x)$, $d_i(x)$ as functions of the duty cycle, length x and width w, of the groove. For constant width, we sweep the duty cycle and obtain the functions, $f_i(x)$ and $d_i(x)$.

Using a plot of the functions, the duty cycle for individual meta surface row can be initialized to satisfy the condition given by, $$f_{i-1} = \frac{d_{i-1}}{t_{i-1}} = d_i \quad \text{(vi)}$$

After the initialization process explained above, the duty cycle of the individual diffracting groove 322 in the metasurface collimator 320 can be tuned to obtain a collimated excitation beam output 305.

Lumerical FDTD software was used to model the way that diffracted power from an individual row increases with an increase in its duty cycle. The spatial distribution of diffracted power and its variance was calculated. The duty cycle of each groove was then tuned to minimize the variance across the rows of the metasurface collimator. Every update in the iterative process was performed as $$C_i = C_i - \delta \frac{P_i - P_{average}}{P_{average}} = C_i - \delta \frac{I_i A_i - I_{average} A_{total}}{I_{average} A}$$

where i is the row number, $\delta$ is the learning rate of the gradient descent method and $P_i$ is the output power calculated by integrating the intensity over the ith row area of meta surface and $P_{average}$ is the average power over the entire meta surface.

With every iteration, the uniformity in the power distribution of the excitation beam collimation may increase. When the duty cycle and the grating period change, the effective index of the structure changes. As a result, the center wavelength of the excitation beam 305 may shift. This may result in poor convergence of the duty cycle in the iterative procedure. Therefore, the central emission wavelength of the excitation beam 305 may be stabilized by modifying the grating period. An additional step may be added to the process to tune the line period ($\Lambda_x$) and stabilize the emission wavelength of the excitation beam 305. Some spatial randomness may be incorporated in each row to avoid lattice diffraction patterns in the profile of the excitation beam 305. This method is wavelength independent and can be used across different photonic materials.

As an example, a metasurface collimator using SiN was designed to operate at C and L bands, the most commonly used wavelength ranges in communication industries.

Figure 4:
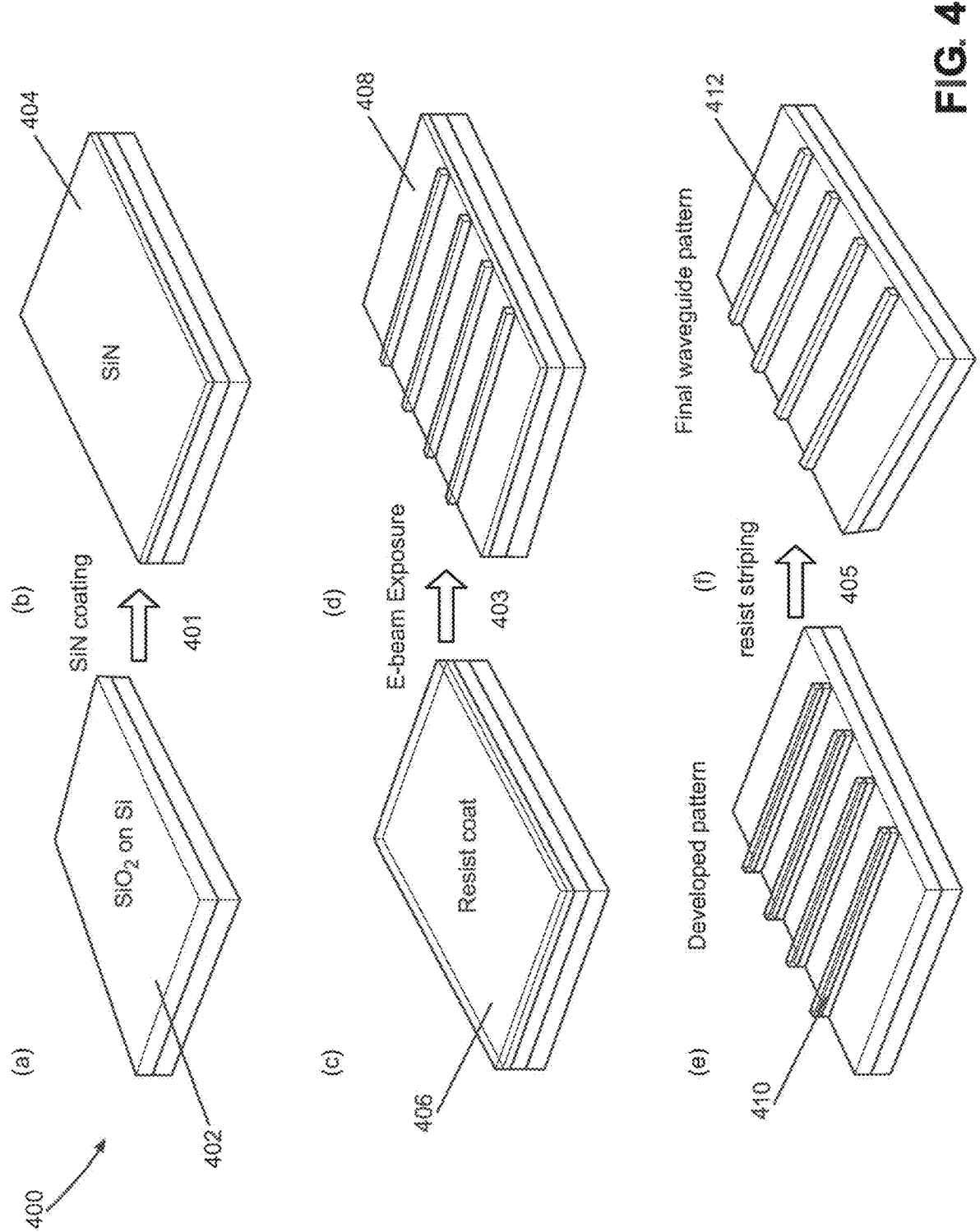
FIG. 4 shows a process for fabricating a waveguide in a PAI sensor.

FIG. 4 shows the steps 400 to fabricate the metasurface collimator. The metasurface collimator may be fabricated by depositing a single layer of patterned SiN 412 on a Si substrate. A low-pressure chemical vapor deposition (LPCVD) system 401 may be used to deposit a 400 nm thick SiN layer 404 onto a 3 μm $SiO_2$ layer 402 on a 6-inch Si substrate. The Si substrates, known as thermal oxide wafers, may be procured from Wafer Pro LLC, CA. The grating structures and waveguides 408 may be patterned via e-beam lithography 403, followed by reactive ion etching to define the geometry of the structures 410. Fluorine chemistry may be used in the dry etching step. After etching, any remaining resist 406 may be stripped 405 using oxygen chemistry and acetone rinsing.

Figure 5:
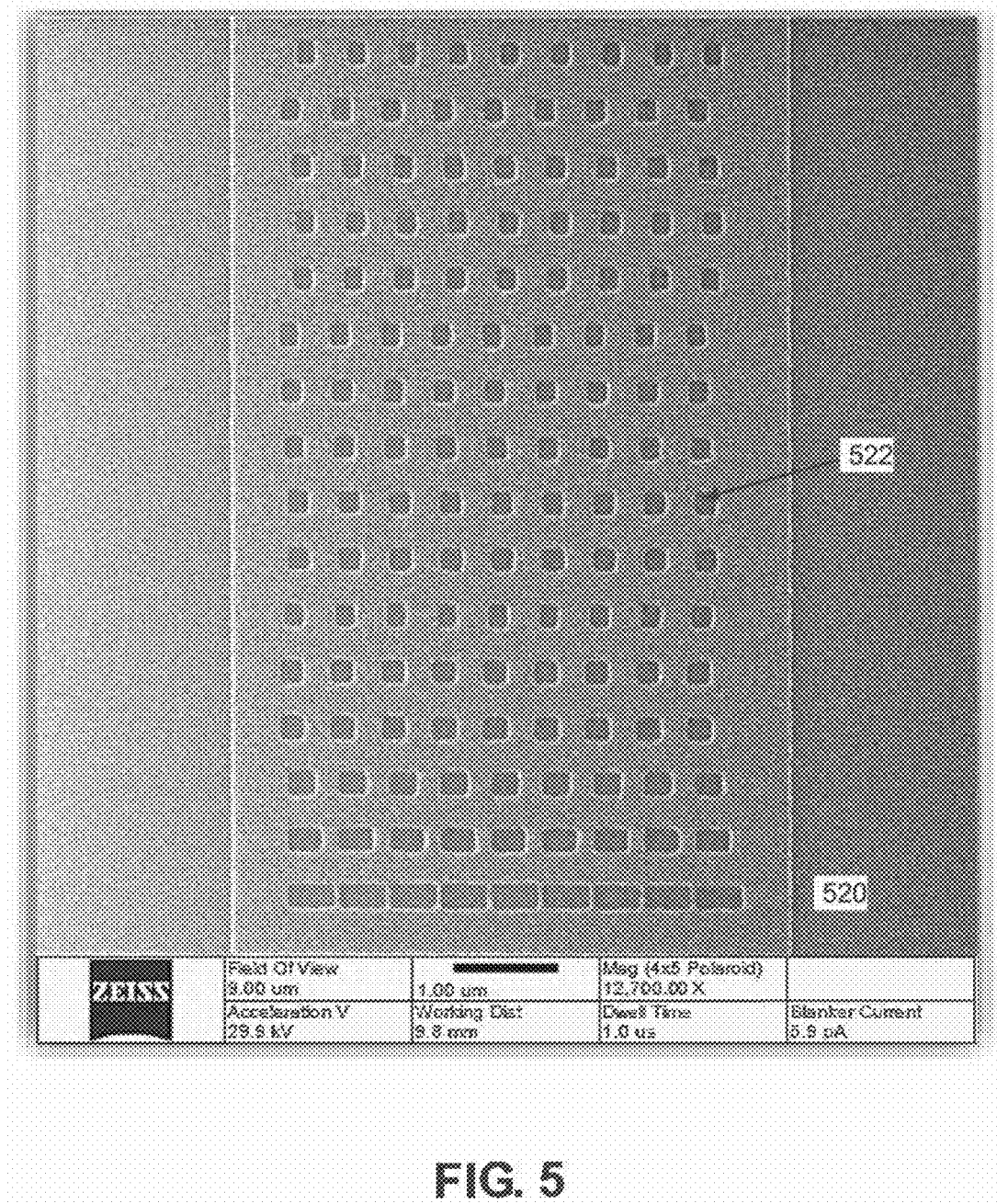
FIG. 5 is an image of a waveguide-based metasurface collimator produced with a scanning electron microscope (SEM).

FIG. 5 shows an SEM image of a metasurface collimator 520 with an array of diffracting grooves 522 that can diffract an excitation beam out of the plane of the metasurface collimator to create a collimated excitation beam. The excitation beam can elicit a photoacoustic signal from an analyte medium.

Figure 6A:
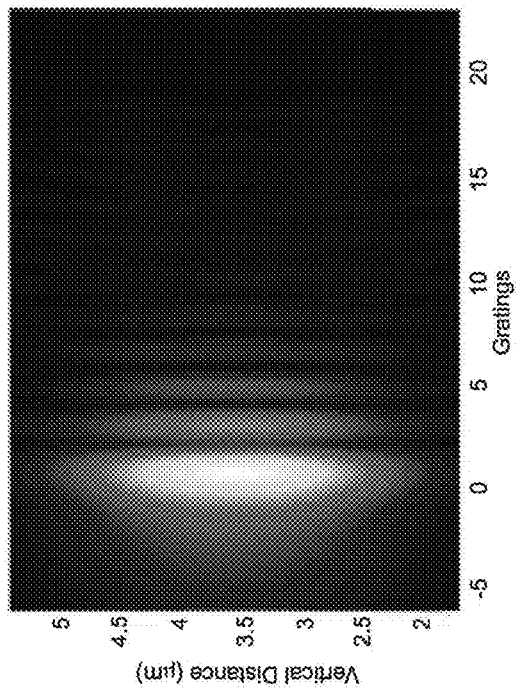
FIG. 6A shows a front view of a simulated emission from a binary grating.
Figure 6B:
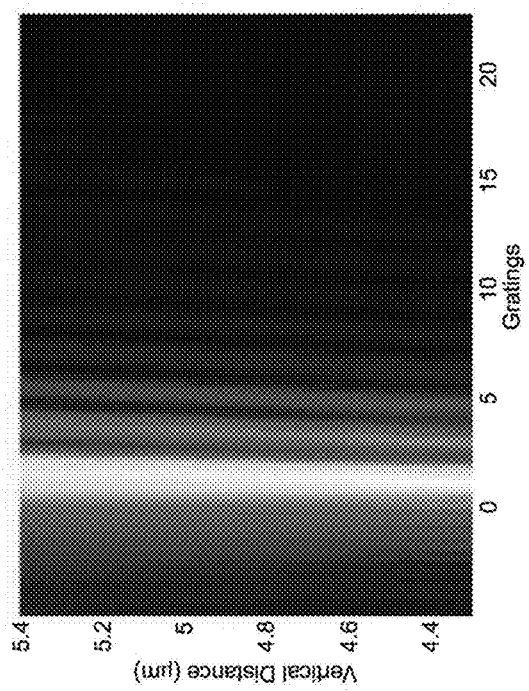
FIG. 6B shows a top view of a simulated emission from the binary grating of FIG. 6A.
Figure 6C:
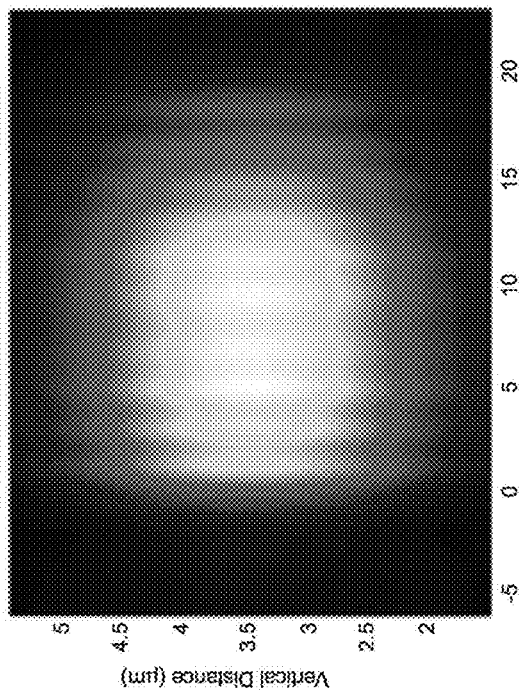
FIG. 6C shows a front view of a simulated emission from a waveguide-based metasurface collimator.
Figure 6D:
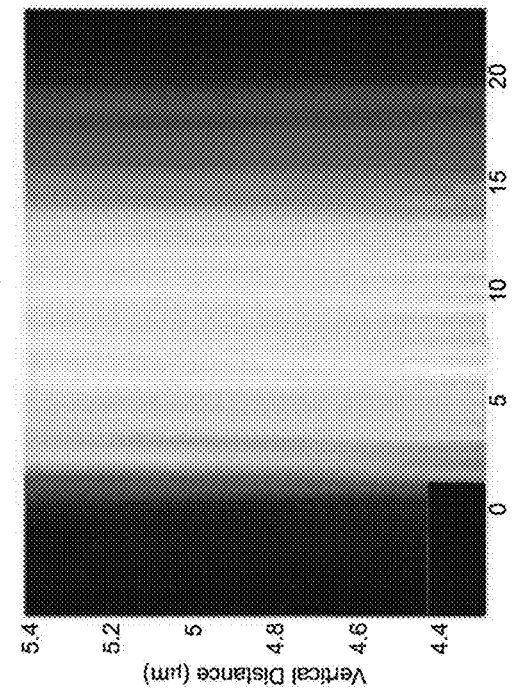
FIG. 6D shows a top view of a simulated emission from the waveguide-based metasurface collimator of FIG. 6C.

FIGS. 6A-6D illustrate how the metasurface collimator may produce a more uniform excitation beam than the excitation beam produced by a binary grating structure. FIGS. 6A and 6B show front and top views, respectively, of a simulated excitation beam exiting from a binary grating. FIGS. 6C and 6D show front and top views, respectively, of a simulated excitation beam exiting from a metasurface collimator. The metasurface collimator produces an excitation beam spot that is larger and more uniform than the spot produced by the binary grating. In a comparison of a binary grating and a metasurface collimator with equal surface areas, the excitation beam spot from the metasurface collimator was 8 times larger in the direction of propagation of the input waveguide. The collimated excitation beam from a metasurface collimator can have an operating bandwidth of about 50 nm.

FIGS. 7A-7D show an experimental analysis of excitation beam profiles from a metasurface collimator and a binary grating structure. FIGS. 7A and 7B show side and top views, respectively, of a 1.0× magnified excitation beam profile from a metasurface collimator. FIGS. 7C and 7D show side and top views, respectively, of a 1.5× magnified excitation beam profile from a binary grating structure. The beam profiles shown in FIGS. 7A-7D were measured using an Agilent 81640A (tunable across C and L band) laser system coupled to an 8164A optical test mainframe. The output of the laser was fiber-coupled terminating with a lensed tip. The lensed tip fibers (with 1 μm working distance) were procured from Nanonics Imaging Ltd. The lensed tip fiber was aligned to either the metasurface collimator or the binary grating structure with a 3-axis stage (XYZ Linear Stage, ULTRAlign) obtained from Newport Inc. A NIR camera from microViewer Inc aligned the fiber tip to the waveguide. During the experimental characterization, a CinCam InGaAs SWI camera (from Axiom Optics, Somerville, Mass.) analyzed the excitation beam profile.

FIGS. 7A-7D show that a metasurface collimator can improve the quality of the excitation beam in several ways. The total power received at the detector that was delivered through the metasurface collimator is approximately 1.4 times higher than that of the binary grating structure. The signal-to-noise ratio (SNR) of illumination from the metasurface collimator was 23 dB. (SNR as used here refers the ratio of the signal when the excitation beam is on to the ambient noise when the excitation beam is off.) The SNR of illumination from the binary grating structure was 15 dB. The binary grating structure has a lower SNR than the metasurface collimator because more energy is lost in scattering and radiation in the binary grating structure. The area of the beam spot from the metasurface collimator was 0.1 $mm^2$, whereas that from the binary grating was 0.06 $mm^2$. The metasurface collimator produced a uniform excitation beam with a width of about 3 dB. The homogeneity of the excitation beam from the metasurface collimator was approximately two times higher than the excitation beam from the binary grating. The metasurface collimator increased the power, SNR, spot size, homogeneity, and illumination efficiency of the excitation beam.

The metasurface collimator may be a component of a microscale optical sensor. The sensor may be placed on a chip for on-chip probing. The metasurface collimator may be an attractive option to couple excitation light from an excitation source and diffract the light out of the plane of the chip. A metasurface collimator may be coupled with an excitation source within a photoacoustic sensor to induce an analyte to produce a photoacoustic signal. However, the metasurface collimator may be designed to work at many different wavelengths of light. A metasurface collimator may be used in on-chip applications of fluorescence imaging, Raman, and IR spectroscopy.

All-Optical Photoacoustic Transducer

FIG. 8 shows a cross-sectional diagram of an optical photoacoustic transducer 800 for the detection of a photoacoustic signal 801. The optical transducer 800 may be a component of a microscale photoacoustic sensor. The optical photoacoustic transducer 800 includes a mechanical membrane 832, a membrane cavity 890, and a resonator 830. The resonator 830 sits on top of the membrane 832. A probe beam produced by a probe light source is evanescently coupled to the resonator 830 via a waveguide 870. The resonator 830 has a resonance frequency that shifts in response to deflection of the membrane 832, where the deflection is caused by the photoacoustic wave 801. The shift of the resonance frequency can be detected by a detector that is coupled to the resonator 830 and a processor can determine the frequency shift detected by the detector.

Photoacoustic sensitivity is defined as the smallest pressure signal that is detectable using a photoacoustic transducer. Photoacoustic sensitivity is defined in terms of the noise level of the detector. Photoacoustic sensitivity is expressed in terms of pressure units and is known as noise equivalent pressure (NEP). Typically, the pressure generated in biological organs or tissues is in the kPa range. An optical photoacoustic transducer can be more sensitive to photoacoustic signals, making it possible to detect weaker signals (e.g., signals from deep tissue). The optical photoacoustic transducer may have a sensitivity ranging from sub-Pa to kPa. For example, the sensitivity of the optical photoacoustic transducer can be as low as 0.2-2.0 mPa/sqrt(Hz). The dynamic range of the photoacoustic transducer can be, e.g., about 100 Pa to about 1 kPa.

The size of the receive aperture, which is set by the size of the membrane, can play a role in determining spatial resolution in photoacoustic transducers. Aperture size also plays a large role in conventional piezoelectric photoacoustic transducers. The spectral bandwidth and resolution of conventional piezoelectric photoacoustic transducers can decrease drastically with decreasing size. In contrast, optical photoacoustic transducers show less of a performance reduction with decreasing size. For example, a piezoelectric photoacoustic transducer with a diameter of 1 mm may have a NEP of about 1.8 kPa and a bandwidth of 16 MHz, while an optical photoacoustic transducer of the same size may have a NEP of about 100 Pa and a bandwidth of about 75 MHz. An optical photoacoustic transducer may respond to photoacoustic signals in a frequency range spanning sub-MHz to 150 MHz. This frequency range may allow an optical photoacoustic transducer to detect absorbing species with a spatial resolution of about 10 µm to about 200 µm.

The NEP of the transducer is affected by the compliance of the membrane, losses in the photonic waveguides, and the quality factor of the ring resonator. The compliance of the membrane is controlled by its thickness and material. Losses in the photonic waveguides result in lower NEP. The frequency of the transducer is controlled by the diameter and thickness of the membrane. Higher frequencies can be detected with membranes with smaller diameters. The bandwidth of the transducer is controlled by the compliance and damping of the materials used in the transducer as well as damping of the surrounding medium.

Finite element modeling can be used to design the optical photoacoustic transducer, the membrane cavity 890 within the optical transducer 800, and the effect of an acoustic pressure wave 801 on a photonic waveguide 870. This finite element analysis can be performed using COMSOL Multiphysics in two steps. The first step investigates structural mechanics of a membrane 832. Structural mechanics studies can be used to design membrane parameters such as diameter and thickness for a given central frequency. The second step investigates the coupling of acoustic wave propagation with optical wave propagation.

The resonant frequency of a membrane depends on its material, diameter, and thickness. The relationship between the size of a membrane and its resonant frequency can be studied using finite element modeling. A parametric sweep of diameter and thickness was performed to obtain eigenfrequencies of a membrane.

Figure 9A:
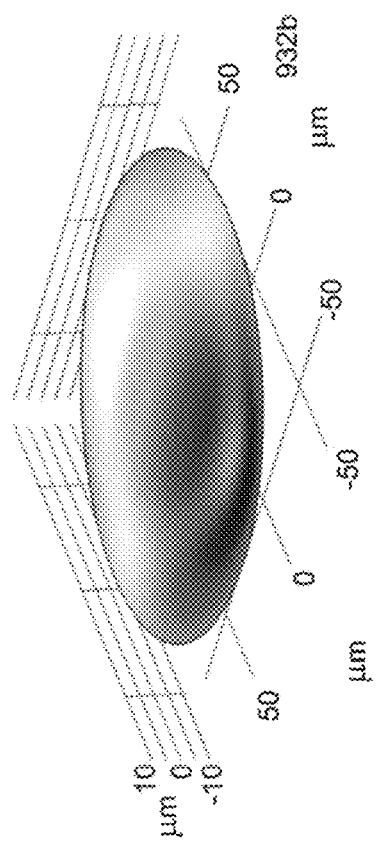
FIG. 9A shows a simulation of a first resonance frequency of a membrane within the photoacoustic transducer of FIG. 8.
Figure 9B:
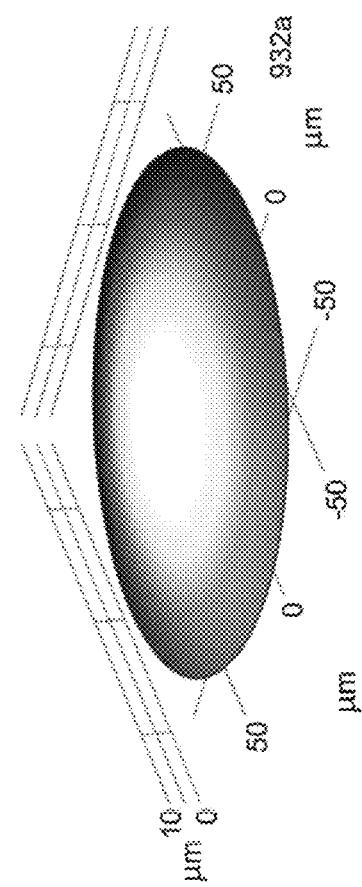
FIG. 9B shows a simulation of a second resonance frequency of a membrane within the photoacoustic transducer of FIG. 8.

FIGS. 9A and 9B show the first and second resonant frequencies, respectively, of an $SiO_2$ membrane with a 90 µm diameter and 3 µm thickness. The first resonant frequency is 1.0 MHz and the second resonant frequency is 2.0 MHz.

Figure 10:
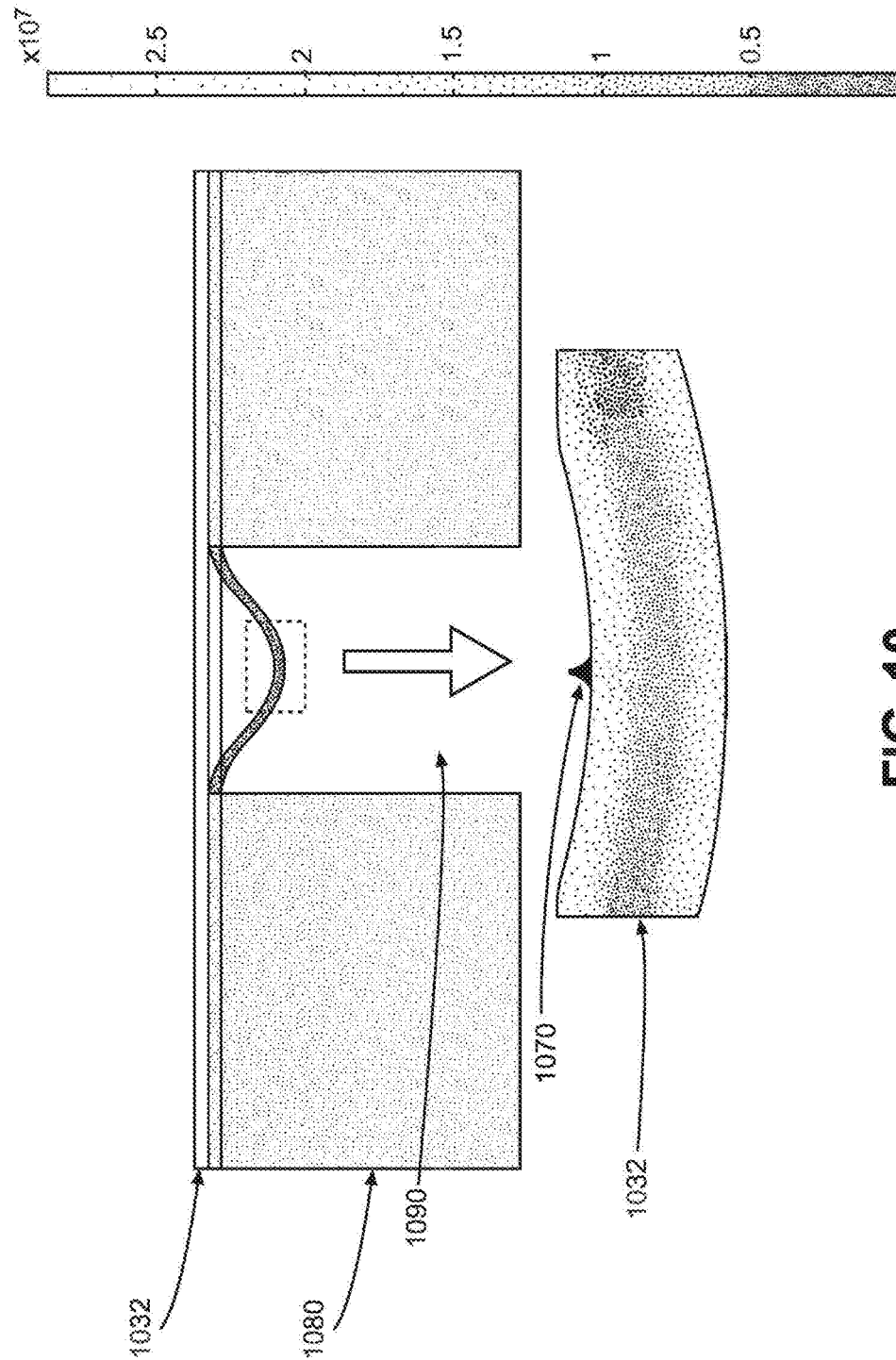
FIG. 10 shows a simulation of a deflection/stress profile of a membrane within the photoacoustic transducer of FIG. 8 with a waveguide on top of it.

The effect of acoustic pressure waves on a membrane can be studied using finite element modeling. FIG. 10 shows the deflection of a membrane 1032 with a photonic waveguide 1070 on top in response to an external pressure wave. For an input pressure of 100 kPa, an $SiO_2$ membrane experienced a stress of $1.64 \times 10^7$ N/m$^2$ and a SiN waveguide on top of the membrane experienced a stress of $4.1 \times 10^5$ N/m$^2$.

Figure 11:
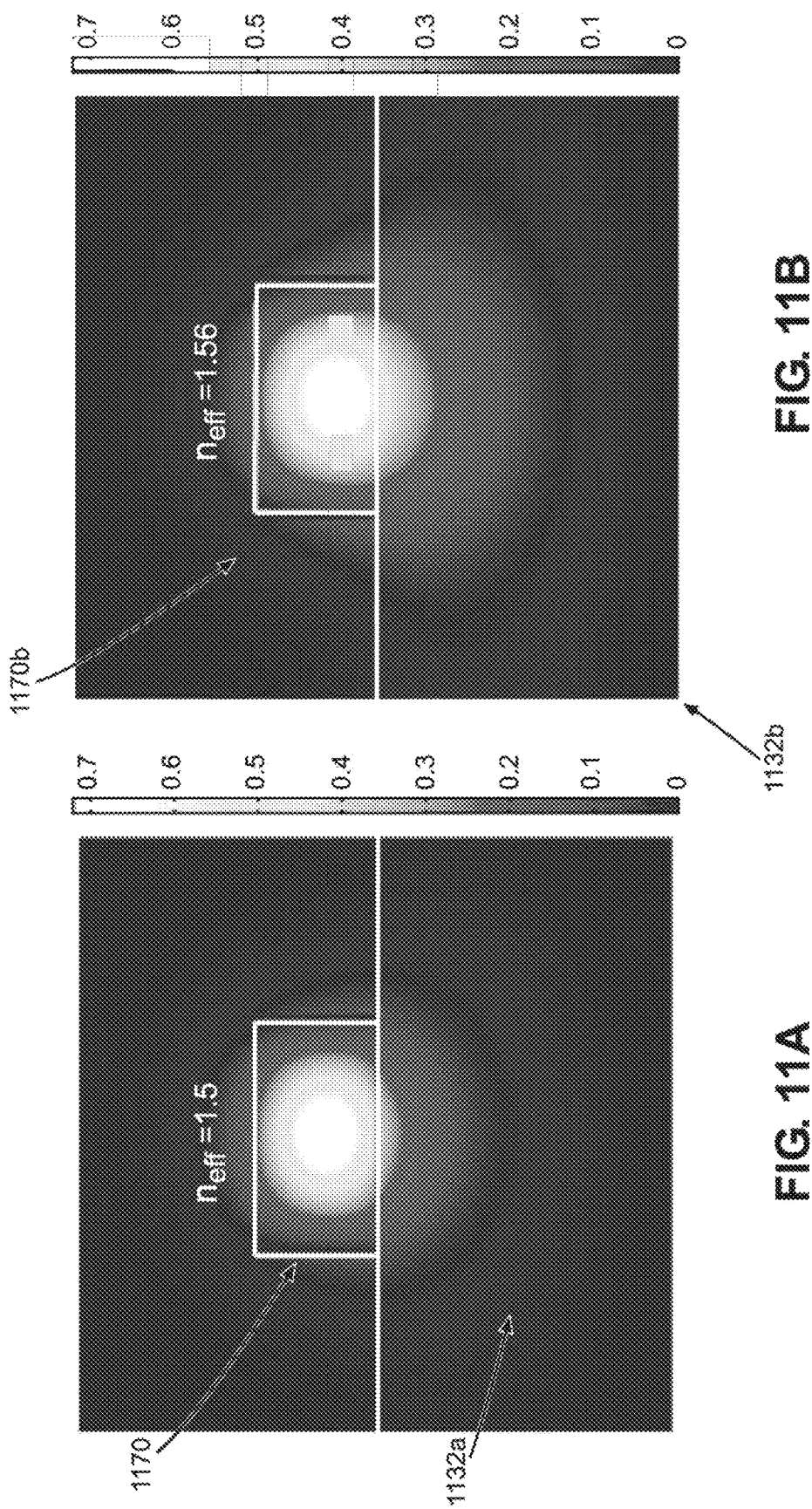
FIG. 11A shows a simulated profile of a mode supported by a photonic waveguide within a photoacoustic transducer before deflection.
FIG. 11B shows a simulated profile of the mode supported by the photonic waveguide within the photoacoustic transducer of FIG. 11A after deflection.

The propagating mode in a photonic waveguide on top of a membrane changes due to the developed stress in the waveguide in response to an external pressure wave. FIG. 11A shows a photonic waveguide 1170a on top of a membrane 1132a at rest. The photonic waveguide 1170a has an effective refractive index of 1.5. FIG. 11B shows a photonic waveguide 1170b on top of a membrane 1132b in response to an external pressure wave. The effective refractive index of the waveguide changes in response to the external pressure wave. The photonic waveguide 1170b has an effective refractive index of 1.56.

Figure 12:
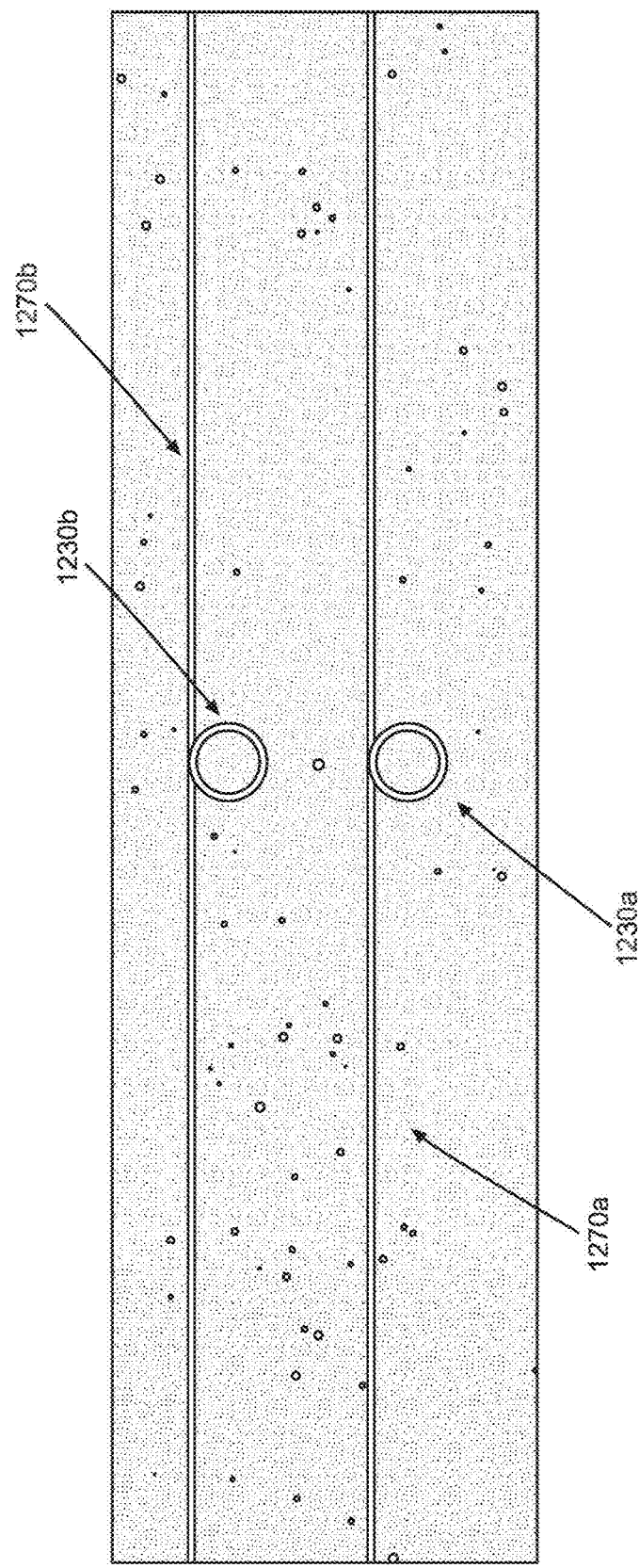
FIG. 12 shows a microscope image of two fabricated photoacoustic transducers.

The change in the mode of a photonic waveguide on top of a membrane in response to an external pressure wave can be monitored with a resonator. Examples of a resonator include a micro ring resonator and a Mach Zehnder interferometer. FIG. 12 shows a microscopic image of two micro ring resonators 1230a and 1230b, and their respective waveguides 1270a and 1270b. These ring resonators each have a diameter of 100 µm and an 800 nm wide waveguide. The ring resonators and waveguides are patterned from 400 nm thick SiN.

Figure 13:
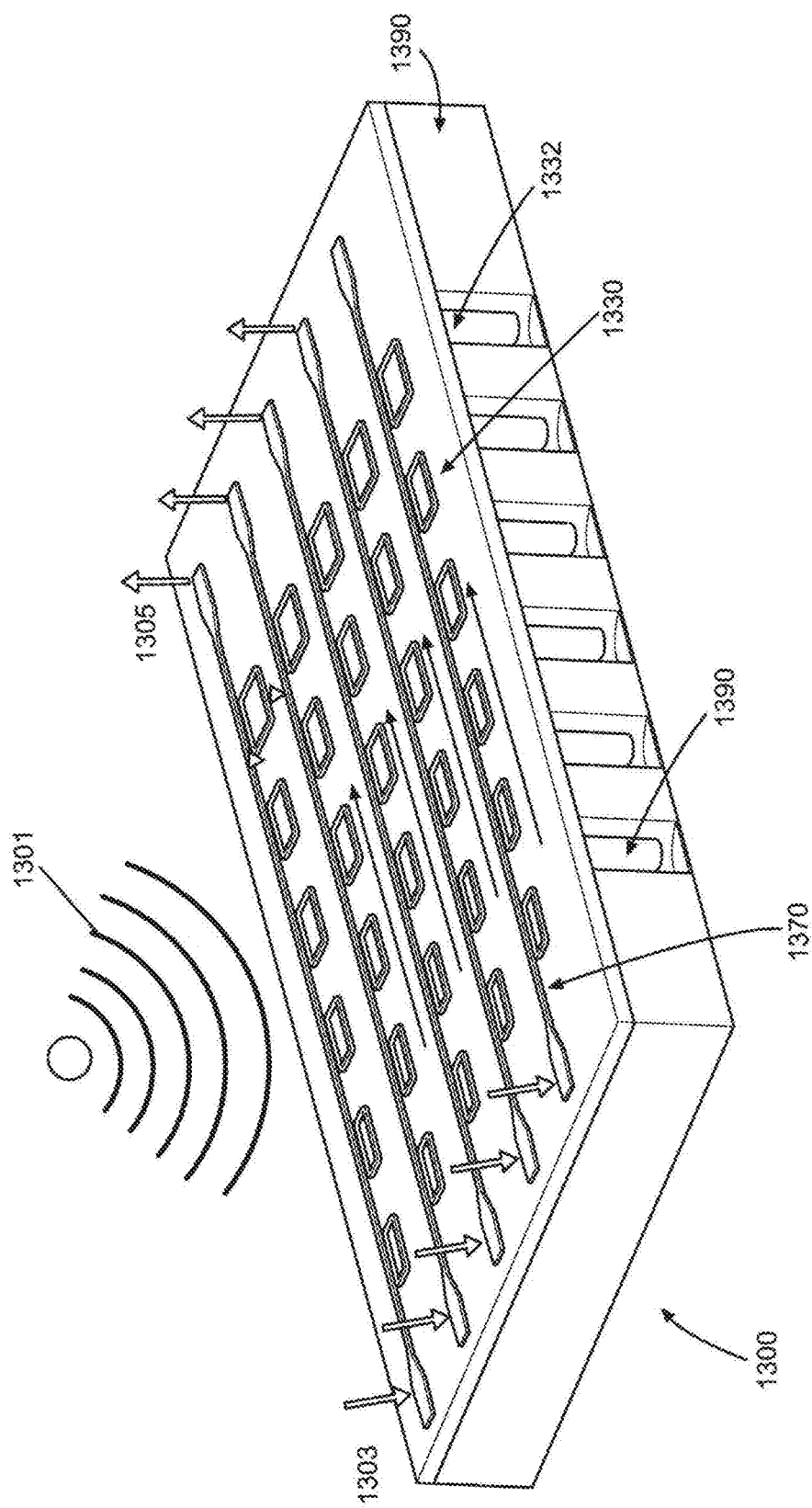
FIG. 13 is a diagram of an array of photoacoustic transducers.

FIG. 13 shows an array of optical photoacoustic transducers 1300 on a chip 1390 for detecting a photoacoustic signal 1301. The array 1300 may be a component of a microscale photoacoustic sensor. Each transducer within the array includes a resonator 1330, a waveguide 1370, a membrane 1332 and a membrane cavity 1390. Waveguides may be coupled to more than one transducer. A probe light source supplies a probe beam 1303 to each waveguide 1370. A shift in the resonance frequency of a resonator 1330 due to a photoacoustic signal can change a property of the probe beam 1305. This change is detected by a detector and processed by a processor to determine a shift of the resonance frequency in response to a photoacoustic signal.

Figure 14:
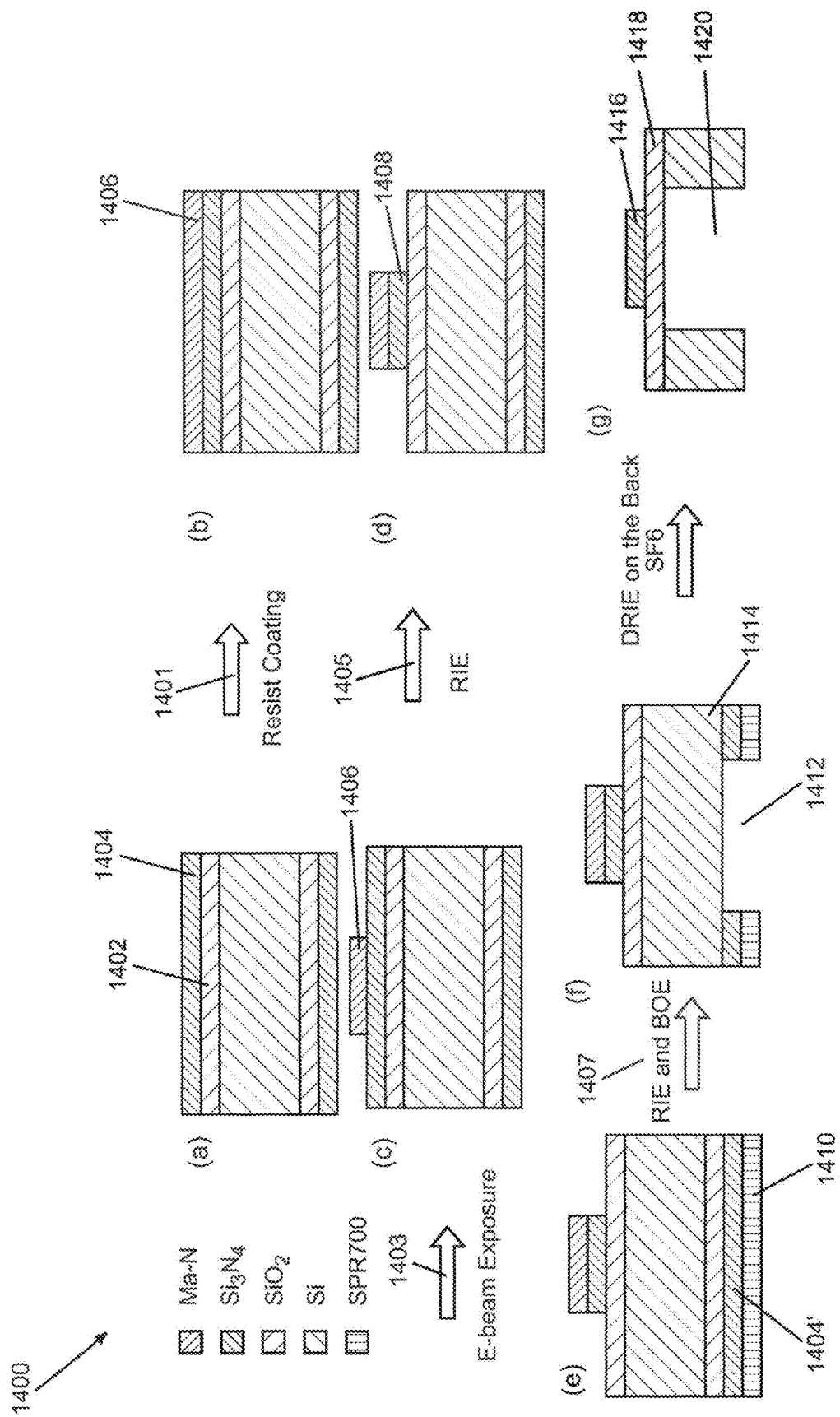
FIG. 14 shows the process to fabricate a photoacoustic transducer.

FIG. 14 shows a procedure 1400 to fabricate an optical photoacoustic transducer. The transducer may be fabricated on a double-sided polished Si wafer. Low pressure CVD (LPCVD) may be used to deposit a layer of $SiO_2$ 1402, followed by a 400 nm thick ultra-low stress SiN layer 1404. Photonic ring resonators and waveguides may be patterned using e-beam lithography. Negative e-beam photoresist 1406 may be coated 1401 and patterned 1403 onto the SiN layer 1404, followed by reactive ion etching 1405 to form waveguide patterns of SiN 1408. After patterning the SiN, a thick layer of photoresist (AZ4620) 1410 may be coated onto the side of the wafer with SiN as a protective layer 1404'. Membrane cavities 1412 are fabricated by patterning circular cavities onto the back side of the wafer using photolithography 1407 with a double-sided alignment procedure using a Maskless Aligner (MLA). Si is etched away using deep reactive ion etching (DRIE) 1409 to create a membrane 1418 and membrane cavity 1420 under the photonic ring resonator structure 1416. The photonic waveguides, ring resonators, and membranes in the microscale photoacoustic sensor can be fabricated using this approach.

Once the components of the sensor have been patterned, the sensor can be patterned into a shape, such as the neural probe shown in FIG. 2A, for release.

Figure 15:
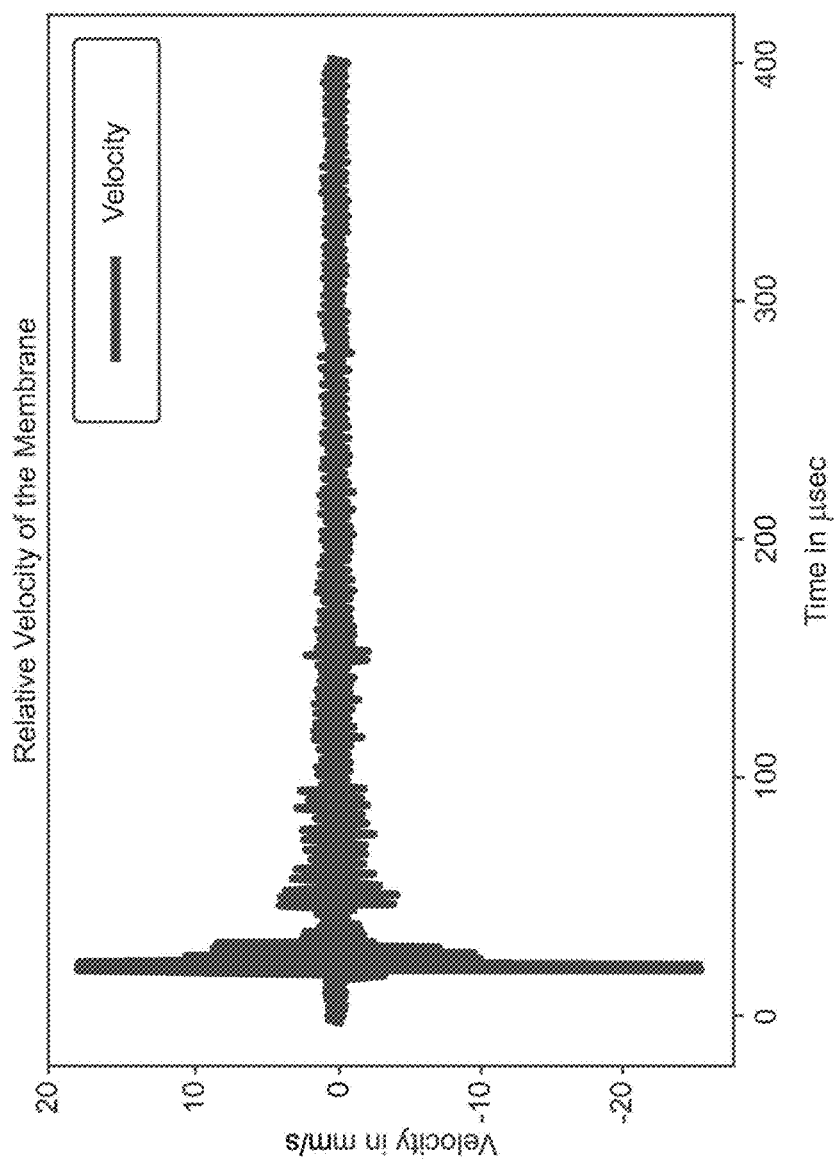
FIG. 15 is a graph of the time series response of the velocity of a deflecting membrane within a photoacoustic transducer with application of an external ultrasound signal of a 1 MHz.

An optical photoacoustic transducer was characterized experimentally in two steps. First, the acoustic performance of a membrane was analyzed using an externally generated ultrasound signal. FIG. 15 shows the transient membrane velocity response of a mechanical membrane as it vibrates acoustically upon exposure to an external pressure of 1 MHz. A laser vibrometer was used to measure the acoustic vibration of the membrane.

Figure 16:
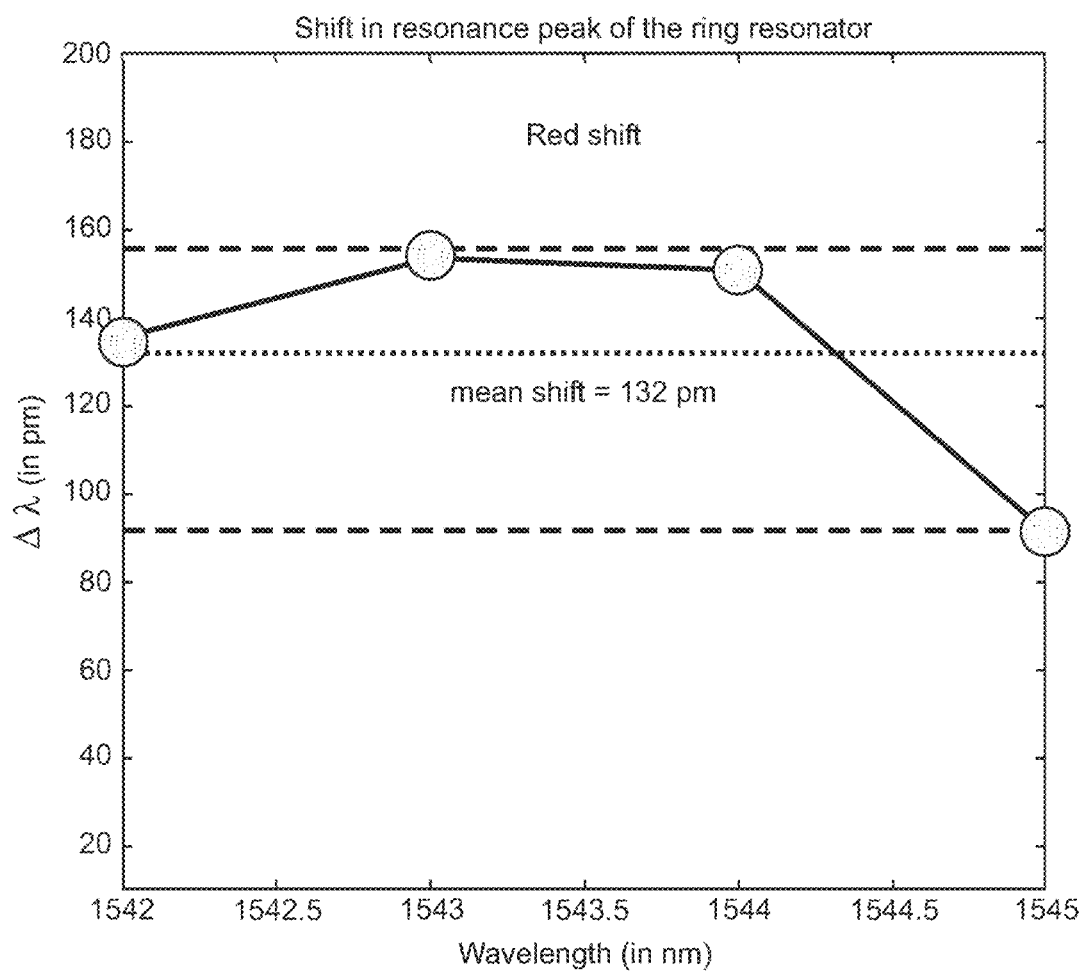
FIG. 16 is a graph of the shift in resonance frequency of a ring resonator within a photoacoustic transducer with and without an external ultrasound signal.

Second, a photonic ring resonator's response to deflection of the mechanical cavity was measured. An external pressure of 1 MHz was used to excite the optical photoacoustic transducer. FIG. 16 shows the shift in the resonance frequency of the ring resonator with and without an external pressure wave. The ring resonator experiences a shift in its optical resonance peak in response to the external pressure wave. The mean shift is about 132 pm. The sensitivity of the optical photoacoustic transducer can be as low as 0.2-2.0 mPa/√Hz.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A sensor comprising:
an excitation light source to emit an excitation beam;
an output coupler, in optical communication with the excitation light source, to couple the excitation beam into an analyte medium, the excitation beam causing the analyte medium to emit a photoacoustic wave;
a first resonator, in acoustic communication with the analyte medium, with a first resonance frequency that shifts in response to the photoacoustic wave;
at least one probe light source, in optical communication with the first resonator, to couple a first probe beam into the first resonator; and
at least one detector, in optical communication with the first resonator, to detect at least a portion of the first probe beam transmitted or reflected by the first resonator; and
a processor, operably coupled to the at least one detector, to determine a shift of the first resonance frequency in response to the photoacoustic wave based on the at least a portion of the first probe beam detected by the at least one detector.

2. The sensor of claim 1, wherein the output coupler comprises a collimator to collimate the excitation beam.

3. The sensor of claim 2, wherein the collimator comprises a meta-surface.

4. The sensor of claim 1, wherein the photoacoustic wave has at least one spectral component in a band from about 1 MHz to about 50 MHz.

5. The sensor of claim 1, wherein the photoacoustic wave has at least one spectral component in a band from about 1 MHz to about 20 MHz.

6. The sensor of claim 1, wherein the first resonator is disposed on a flexible membrane configured to deflect in response to the photoacoustic wave.

7. The sensor of claim 1, wherein the first resonator comprises a polymer ring resonator.

8. The sensor of claim 1, further comprising:
a second resonator, in acoustic communication with the analyte medium and in optical communication with the at least one probe light source and the at least one detector, with a second resonance frequency that shifts in response to the photoacoustic wave.

9. The sensor of claim 8, wherein the second resonance frequency is different than the first resonance frequency.

10. The sensor of claim 8, wherein the at least one probe light source is configured to couple a second probe beam into the second resonator, the at least one detector is configured to detect at least a portion of the second probe beam transmitted or reflected by the second resonator, and the processor is configured to determine a shift of the second resonance frequency in response to the photoacoustic wave based on the at least a portion of the second probe beam detected by the at least one detector.

11. The sensor of claim 10, where the processor is configured to determine a temporal shift between the shift in the first resonance frequency and the shift in the second resonance frequency.

12. The sensor of claim 1, wherein the first resonator is disposed on a membrane that vibrates in response to the photoacoustic wave, and the membrane is at least partially disposed above a cavity.

13. The sensor of claim 1, further comprising:
a microfluidic channel, in optical communication with the output coupler and the first resonator, to flow the analyte medium past the output coupler and the first resonator.

14. The sensor of claim 1, further comprising:
a substrate,
wherein the output coupler and the first sensor are disposed on a surface of the substrate.

15. The sensor of claim 1, wherein the excitation beam has a center wavelength of about 1530 nm to about 1565 nm.

16. A neurophotonic probe comprising:
a substrate with a tip for penetrating neural tissue;
probe ring resonators, along the tip of the substrate, having respective resonance frequencies that shift in response to acoustic excitation;
at least one input waveguide, on the substrate and evanescently coupled to the probe ring resonators, to couple probe light into the ring resonators; and
at least one output waveguide, on the substrate and evanescently coupled to the probe ring resonators, to couple probe light out of the probe ring resonators.

17. The neurophotonic probe of claim 16, wherein at least a portion of the tip of the substrate is configured to deflect in response to the acoustic excitation, thereby shifting the respective resonance frequencies of the probe ring resonators.

18. The neurophotonic probe of claim 16, further comprising:
wavelength-division multiplexing (WDM) ring resonators, evanescently coupled to the at least one output waveguide and a bus waveguide, to couple the probe light from the at least one output waveguide to the bus waveguide.

19. A method of imaging neural tissue, the method comprising:
inserting a neural probe into the neural tissue;
measuring a shift in a resonance frequency of a first optical ring resonator on the neural probe caused by a photoacoustic excitation propagating through the neural tissue; and
generating an image of the neural tissue based at least in part on the shift in resonance frequency of the first optical ring resonator.

20. The method of claim 19, wherein generating the image comprises generating the image with a spatial resolution of about 20 microns to about 50 microns.

21. The method of claim 19, wherein generating the image comprises generating the image over a volume of about 1 cubic millimeter.

22. The method of claim 19, further comprising:
measuring a shift in a resonance frequency of a second optical ring resonator on the neural probe caused by the photoacoustic excitation propagating through the neural tissue.

23. The method of claim 19, further comprising:
illuminating the neural tissue with a probe beam to produce the photoacoustic excitation propagating through the neural tissue.

* * * * *